(12) United States Patent
Sato et al.

(10) Patent No.: US 8,271,250 B2
(45) Date of Patent: Sep. 18, 2012

(54) MOLECULE DESIGN SUPPORT APPARATUS AND COMPUTER-READABLE STORAGE MEDIUM

(75) Inventors: Hiroyuki Sato, Kawasaki (JP); Azuma Matsuura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1323 days.

(21) Appl. No.: 11/976,360

(22) Filed: Oct. 24, 2007

(65) Prior Publication Data

US 2008/0120575 A1 May 22, 2008

(30) Foreign Application Priority Data

Nov. 16, 2006 (JP) ................................. 2006-310564

(51) Int. Cl.
*G06G 7/58* (2006.01)
(52) U.S. Cl. ........................................................ 703/11
(58) Field of Classification Search ...................... 703/11
See application file for complete search history.

(56) References Cited

U.S. PATENT DOCUMENTS 5,572,439 A * 11/1996 Nishida et al. .................. 702/27
6,185,472 B1    2/2001 Onga et al.

FOREIGN PATENT DOCUMENTS

| JP | 5-120396 A | 5/1993 |
| JP | 5-128218 A | 5/1993 |
| JP | 5-174109 A | 7/1993 |
| JP | 8-173155 A | 7/1996 |
| JP | 2006-196908 A | 7/2006 |

OTHER PUBLICATIONS

Makoto Ando, "Parallel Tree Search-based Protein Conformation Implemented on a Massively Parallel Computer", Information Transactions on Mathematical Modeling and Its Applications, SIG 2 (TOM 1), pp. 91-104.

Hashimoto, J., et al., "Effects of a sulfur substituent on the behavior and generation mode of aroyloxyl radicals in the photolysis of diaroyl peroxides", Chemical Physics Letters, Dec. 3, 1999, pp. 26 261-266, vol. 314 (1999), Elsevier Science B.V.

* cited by examiner

*Primary Examiner* — Jerry Lin
(74) *Attorney, Agent, or Firm* — Fujitsu Patent Center

(57) ABSTRACT

A molecule design support apparatus has an input part, a display to display on a screen thereof a three-dimensional molecular structure by a half vector format or a ball-and-stick format, and a determining part to determine, in the molecular structure, an end that is to become a target of a coordinate modification with respect to a molecule in its entirety, in response to a bond axis of the molecule specified from the input part. The apparatus further has a modifying part to make a modification of the molecular structure based on the specified bond axis and the end that is the target of the coordinate modification, in response to the modification specified from the input part, and a display part to display a modified molecular structure on the screen of the display based on a determination made by the determining part and the modification made by the modifying part.

18 Claims, 36 Drawing Sheets

SELECTION: B2, A3
RING FLAG: FALSE
FIXED END: A3
TARGET AXIS: B1, B2, B3
ROTATION INFORMATION:
SCREEN OPERATION

ROTATION
COMPUTATION: $R$
$B'1 = R\, B1$
$B'2 = R\, B2$
$B'3 = R\, B3$

COORDINATE
MODIFICATION: A1,A2,A4
$A'1 = A3 + B'2$
$A'2 = A'1 + B'1$
$A'4 = A'1 + B'3$

SELECTION: B2, A3
RING FLAG: FALSE
FIXED END: A3
TARGET AXIS: B2

EXPANSION & CONTRACTION
COMPUTATION: S
B'2=$\underline{S}$ B2

COORDINATE
MODIFICATION: A1, A2, A4
A'1=A3+B'2
A'2=A'1+B1
A'4=A'1+B3

MOLECULE DESIGN SUPPORT APPARATUS AND COMPUTER-READABLE STORAGE MEDIUM

BACKGROUND OF THE INVENTION

1. Field of the Invention

The present invention generally relates to molecule design support apparatuses and computer-readable storage media, and more particularly to a molecule design support apparatus for making a three-dimensional display of a molecular structure and performing a molecular structure assembling operation and to a computer-readable storage medium that stores a program for causing a computer to carry out such a molecular structure assembling operation.

The molecular design support apparatus and the computer-readable storage medium according to the present invention include Graphical User Interfaces (GUIs) and molecular design support tools.

2. Description of the Related Art

Due to the realization of high-performance computer systems, there are increased demands to make theoretical chemistry computations, such as computations of molecular orbits and molecular dynamics, in research of advanced technologies such as drug design. In order to execute such theoretical chemistry computations, it is necessary to use, as input data, not only the computation method but also the structure of the molecule that is the computation target. In the research of advanced technologies such as drug design, it is often necessary to search for a new molecular structure that can improve the effects of the property such as the polarizability, and for this reason, there are increased demands to assemble an arbitrary molecular structure. In order to satisfy such demands and to improve the work efficiency when assembling the molecular structure, various molecule design systems utilizing the graphic display function have been proposed. For example, Japanese Laid-Open Patent Applications No. 5-174109 and No. 5-128218, and http://software.fujitsu.com/jp/products/indust11.html, WinMOPAC (Fujitsu Limited) and CAChe (Fujitsu Limited) propose such molecule design systems.

The conventional technique for modifying the molecular structure tolerates, in most cases, a modification of only a bond direction that is determined for each type of atom, thereby inhibiting an arbitrary modification of the molecular structure. In addition, in a molecular structure assembling system which enables an arbitrary modification of the molecular structure, similarly to the GUI of the WinMOPAC manufactured by Fujitsu Limited, when internal coordinates of the molecule called the Z-matrix are used, only the bond angle and the dihedral angle included in the internal coordinates become the modifying targets. But because only the dihedral angle can be set from one direction in the internal coordinates, it is difficult to easily make an arbitrary modification of the molecular structure. In addition, in the molecular structure assembling system typified by the WinMOPAC, when a rotation operation is made with respect to the molecular structure having the ring structure, a portion that participates in the rotation and a portion that does not participate in the rotation become connected due to the ring formed thereby, and there was a problem in that a desired molecular structure cannot be obtained in many cases because the portion that was not intended to be modified is actually modified by the operation.

SUMMARY OF THE INVENTION

One object of the present invention is to provide a molecule design support apparatus including an input part; a display configured to display on a screen thereof a three-dimensional molecular structure by a half vector format or a ball-and-stick format; a determining part configured to determine, in the molecular structure, an end that is to become a target of a coordinate modification with respect to a molecule in its entirety, in response to a bond axis of the molecule specified from the input part; a modifying part configured to make a modification of the molecular structure based on the specified bond axis and the end that is the target of the coordinate modification, in response to the modification specified from the input part, said modification including at least one of a free rotation around an atom, a rotation around a bond axis, an angular modification between two axes, a modification of a dihedral angle, and an expansion and contraction of a bond axis; and a display part configured to display a modified molecular structure on the screen of the display based on a determination made by the determining part and the modification made by the modifying part. According to the molecule design support apparatus of the present invention, it is possible to easily execute a desired molecular structure modifying operation, without being affected by an initial structure and initial coordinates, and without resulting in an unintended structure.

Another object of the present invention is to provide a computer-readable storage medium which stores a program for causing a computer, having an input part, to realize a molecule design support function, said program including a determining procedure causing the computer to determine, in a three-dimensional molecular structure that is displayed by a half vector format or a ball-and-stick format on a screen of a display, an end that is to become a target of a coordinate modification with respect to a molecule in its entirety, in response to a bond axis of the molecule specified from the input part; a modifying procedure causing the computer to make a modification of the molecular structure based on the specified bond axis and the end that is the target of the coordinate modification, in response to the modification specified from the input part, said modification including at least one of a free rotation around an atom, a rotation around a bond axis, an angular modification between two axes, a modification of a dihedral angle, and an expansion and contraction of a bond axis; and a display procedure causing the computer to display a modified molecular structure on the screen of the display based on a determination made by the determining procedure and the modification made by the modifying procedure. According to the computer-readable storage medium of the present invention, it is possible to easily execute a desired molecular structure modifying operation, without being affected by an initial structure and initial coordinates, and without resulting in an unintended structure.

Other objects and further features of the present invention will be apparent from the following detailed description when read in conjunction with the accompanying drawings.

DESCRIPTION OF THE PREFERRED EMBODIMENTS

Figure 1:
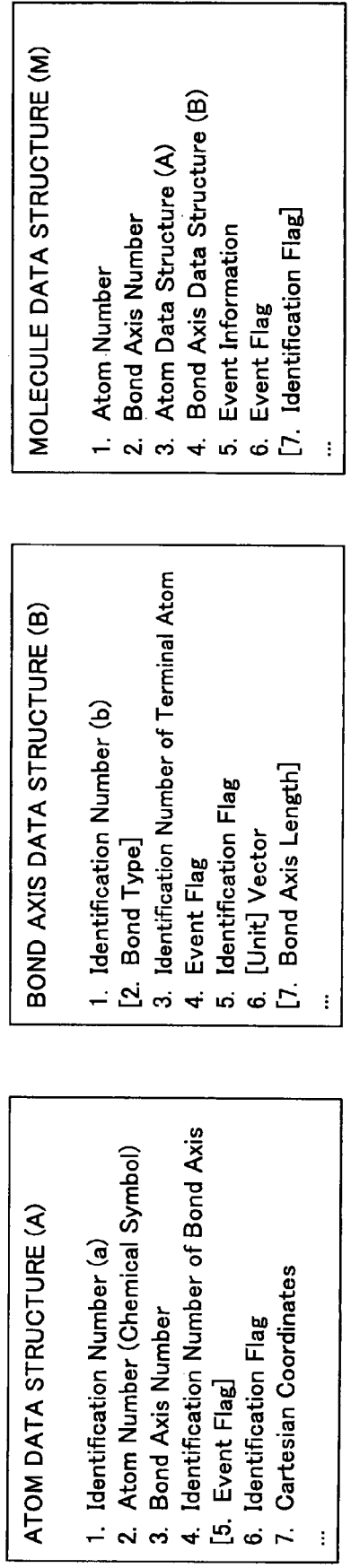
FIG. 1 is a diagram for explaining data structures.

When making a molecular structure modifying operation in the present invention, the data structures shown in FIG. 1, that is, an atom data structure A, a bond axis data structure B and a molecule data structure M, are used. In the data structures shown in FIG. 1, the atom data structure A and the bond axis data structure B respectively differ from the conventionally used data structures in that both include data corresponding 1:1 with respect to all of the atoms and the bond axes, and in that both include an event flag and an identification flag. In FIG. 1, numerals 1, 2, ..., 7, ... are assigned to each of the constituent elements (or items) of each of the data structures A, B and M, and data in brackets "[ ]" indicate that the data are not essential.

In the atom data structure A, an identification number "a" is made up of an atomic sequence number in the internal coordinates, and an atom number (or number of atoms) is made up of the chemical symbol. A bond axis number (or number of bond axes) is made up of a numerical value that varies when an arbitrary new molecular structure is added to the original molecule. An initial value of the bond axis number indicates the bond number that is estimated from an input structure as forming the atom pair based on the van der Waals radius. The identification number of the bond axis is made up of a set data of an identification number "b" of each bond axis included in the bond axis number. The event flag indicates the present type of event with respect to the events of the molecular structure forming GUI, such as a rotation operation, an expansion and contraction operation, a delete operation, an add operation and a replace operation. The identification flag is used to check whether or not the molecular structure has a ring structure, in order to prevent an unintended structure from being obtained. Cartesian coordinates are made up of data indicating a position within a three-dimensional space where each atom is located.

In the bond axis data structure B, the identification number "b" is made up of the number that is necessary to make all of the bond axes correspond 1:1 with each other. A bond type is made up of data identifying the type of bond axis, such as the single bond and the double bond. When forming an arbitrary molecular structure, the bond type is not essential. An identification number of the terminal atom is made up of a set data of the identification number "a" of the atom existing at both terminals of the bond axis, and a data number is 2. The event flag and the identification flag are the same as the event flag and the identification flag of the atom data structure A. Vector information includes information indicating a 1:1 correspondence between the bond axis and a three-dimensional vector. When representing the vector information by a unit vector, it is also necessary to include in the bond axis data structure B a bond axis length that indicates the length of the bond axis.

The molecule data structure M includes both the atom data structure A and the bond axis data structure B that hold mutual data. In order to cope with the delete operation and the add operation, the molecule data structure M includes the atom number, the bond axis number, event information and the event flag. The molecule data structure M may include the identification flag if necessary.

Figure 2:
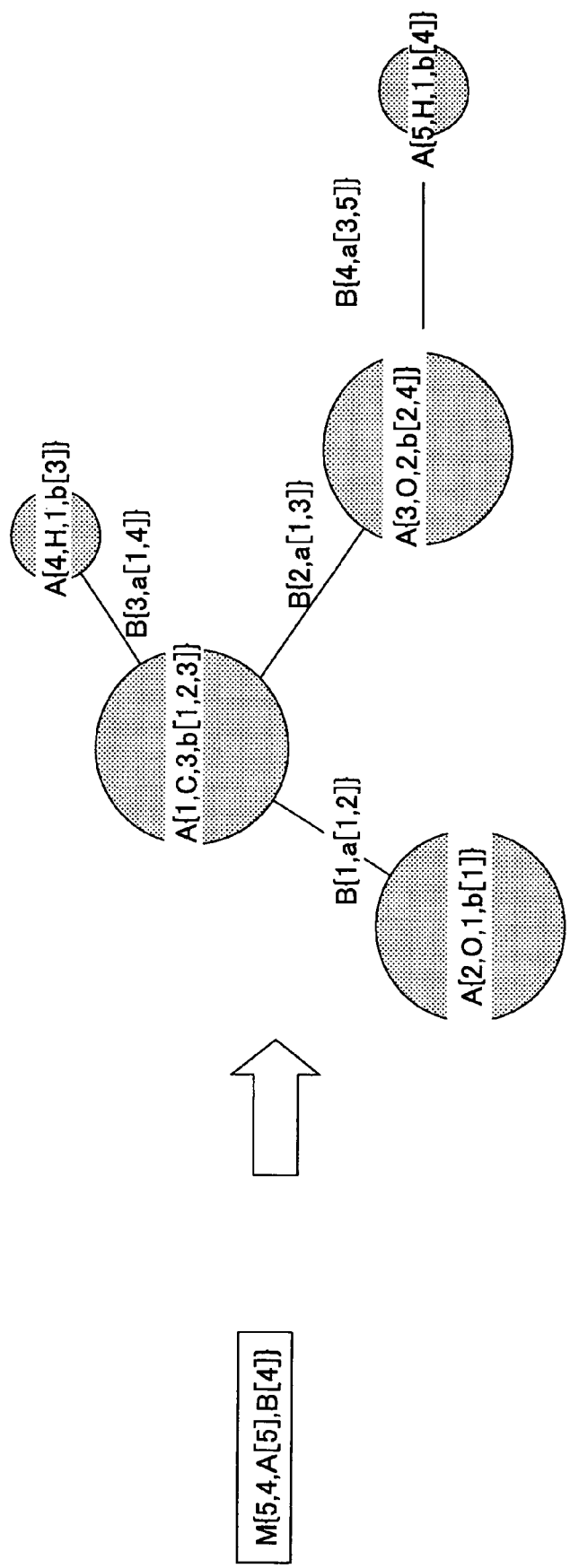
FIG. 2 is a diagram for explaining how the data structure is set by taking formic acid (HCOOH) as an example.

A description will be given of how the data structures shown in FIG. 1 are set when the data of the molecular structure are given, in conjunction with FIG. 2, by taking formic acid (HCOOH) as an example. In FIG. 2, "A{ }" indicates the atom data structure A, "B{ }" indicates the bond axis data structure B, and "M{ }" indicates the molecule data structure M. In addition, "a[ ]" is an array that holds the identification number of the bond axis included in the bond axis data structure B, and the array number is 2. Further, "b[ ]" indicates an array that holds the identification number of the bond axis included in the atom data structure A, and the array number is the bond axis number included in the atom data structure A. The chemical symbol data included in the atom data structure A may be the atom number. Hence, for the sake of convenience, FIG. 2 shows the item numbers 1 to 4 of the atom data structure A, the item numbers 1 and 3 of the bond axis data structure B, and the item numbers 1 to 4 of the molecule data structure M.

Figure 3:
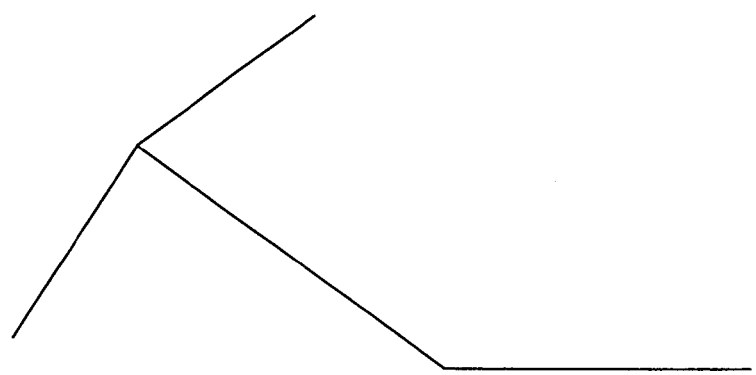
FIG. 3 is a diagram for explaining a half vector format display.
Figure 4:
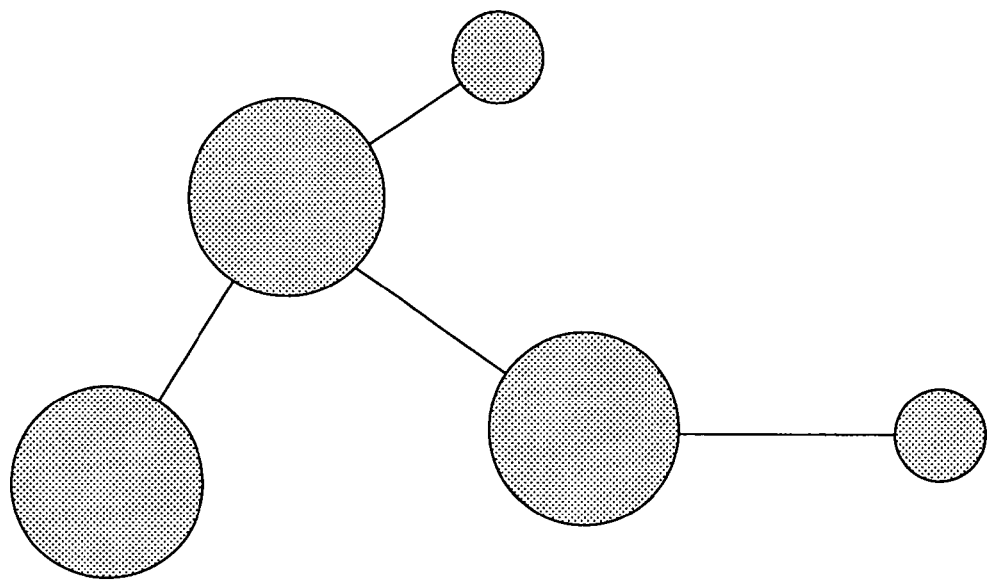
FIG. 4 is a diagram for explaining a ball-and-stick format display.

When making the molecular structure modifying operation, a main window for work is displayed on a screen of a display, for example, and a three-dimensional molecular structure is displayed in the main window with a half vector format shown in FIG. 3 or a ball-and-stick format shown in FIG. 4. By making an operation from an input part, such as clicking a pointing device, making a drag-and-drop operation of the pointing device and operating a keyboard, at least one bond axis of the molecule is displayed in the main window. If necessary, one of two terminal atoms of the bond axis is specified in the ball-and-stick format so as to further determine the end (or side) that becomes the target of the coordinate modification with respect to the bond axis, and a continuous modifying operation of the molecular structure, such as a free rotation around the atom, a rotation around the bond axis, an angle modification between two axes, a modification of the dihedral angle, and expansion and contraction of the bond axis, so as to display the newly formed molecular structure in the main window.

Accordingly, it is possible to easily execute a desired molecular structure modifying operation, without being affected by the initial structure and the initial coordinates, and without resulting in an unintended structure.

Figure 5:
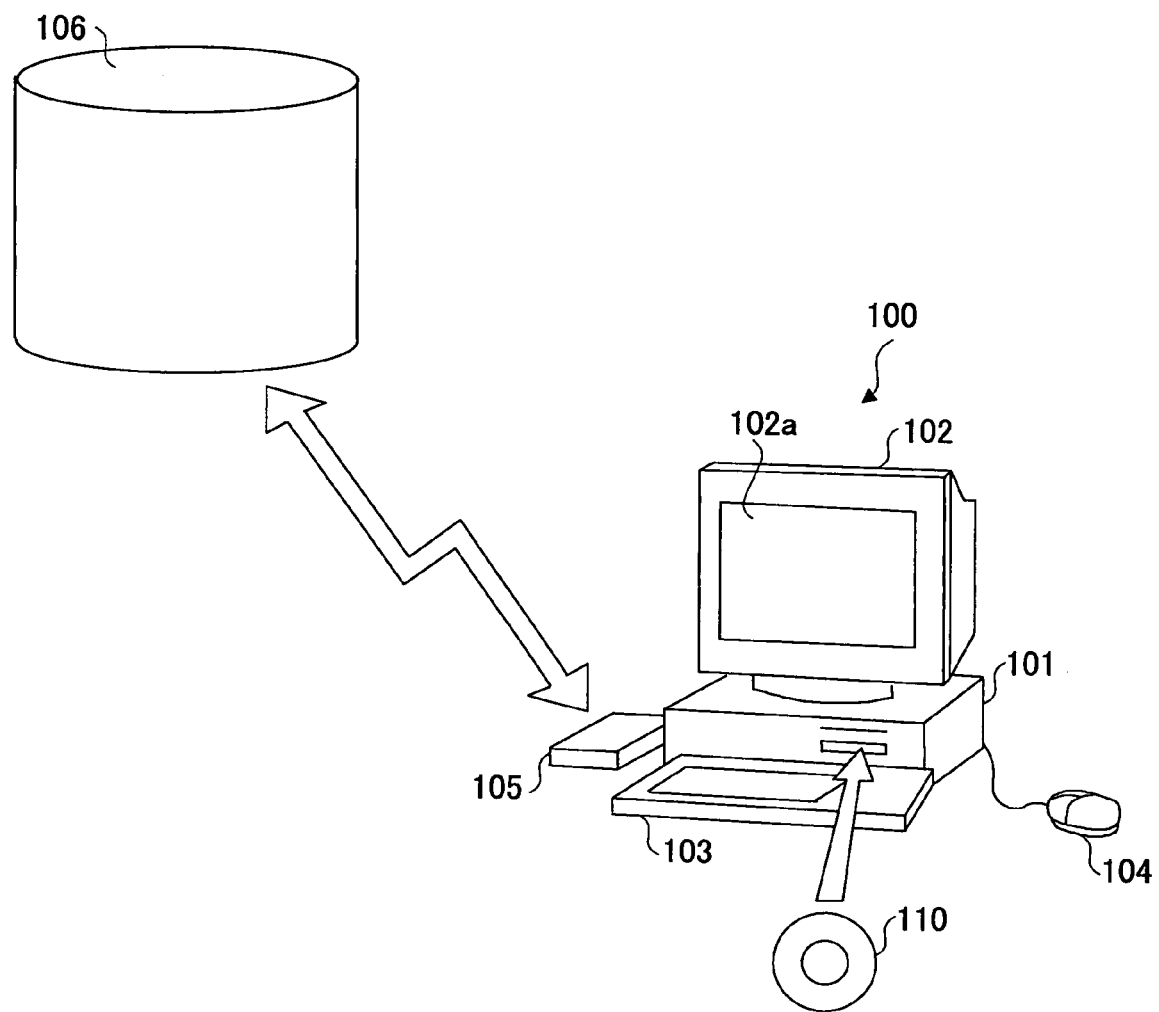
FIG. 5 is a perspective view showing a computer system applied with the present invention.

An embodiment of the molecule design support apparatus according to the present invention may employ an embodiment of the computer-readable program according to the present invention. The computer-readable program may be stored in an embodiment of the computer-readable storage medium according to the present invention. In this embodiment, the present invention is applied to a computer system. FIG. 5 is a perspective view showing a computer system applied with the present invention.

A computer system 100 shown in FIG. 5 includes a main body 101 that has a built-in CPU, disk drive and the like, a display 102, a keyboard 103, a mouse 104, and a modem 105. The display 102 has a display screen 102a on which images of molecules and the like formed by a molecule forming simulation are displayed in response to an instruction from the main body 101. The keyboard 103 is used to input various information to the computer system 100. The mouse 104 is used to specify an arbitrary position on the display screen 102a of the display 102. The modem 105 is used to make access to an external database or the like and to download programs and the like stored in other computer systems.

A program (molecule design support software or tool) for causing the computer system 100 to have at least a molecule design support function, is input to the computer system 100 and compiled therein. This program of the present invention may be stored in a portable recording medium such as a disk 110 or, downloaded from a recording medium 106 of another computer system using a communication apparatus such as the modem 105. This program causes the computer system 100 (that is, a CPU 201 which will be described later) to operate as a molecule design support apparatus (or a simulation system) having the molecule design support function. This program may be stored in this embodiment of the computer-readable storage medium, such as the disk 110. The computer-readable storage medium is not limited to portable recording media such as the disk 110, IC card memories, magnetic disks such as floppy disks, magneto-optical disks and CD-ROMs, and includes various recording media that are accessible by a computer system which is connected to the computer system 100 via the communication apparatus or communication means such as the modem 105 and the LAN.

Figure 6:
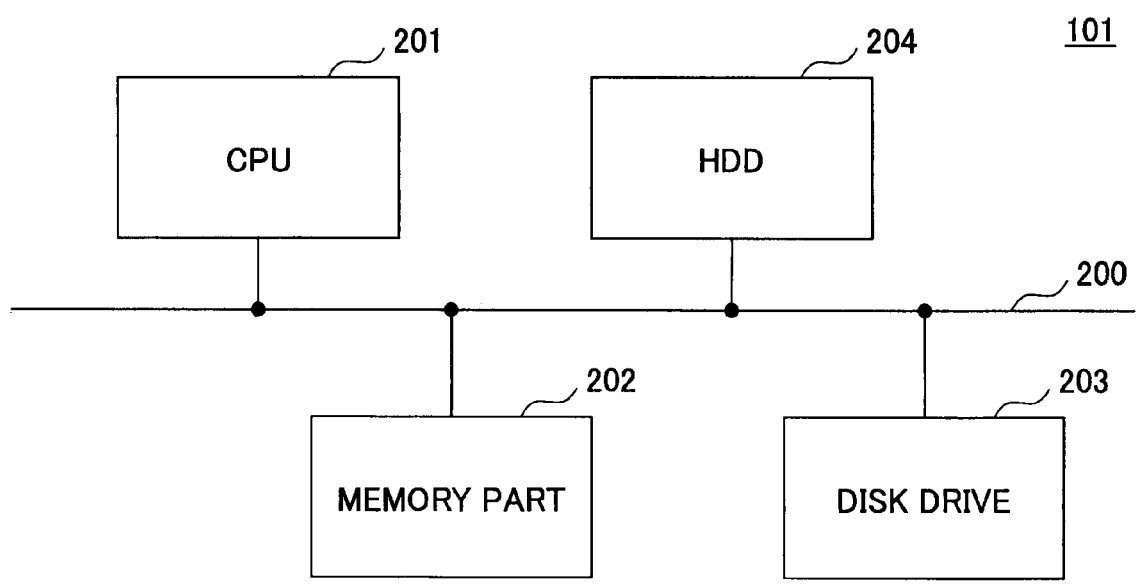
FIG. 6 is a system block diagram showing a structure of an important part of a main body within the computer system.

FIG. 6 is a system block diagram showing a structure of an important part of the main body 101 within the computer system 100. The main body 101 has the CPU 201, a memory part 202 made up of a RAM, a ROM and the like, a disk drive 203 for the disk 110, and a Hard Disk Drive (HDD) 204 that are connected via a bus 200. In this embodiment, the display 102, the keyboard 103 and the mouse 104 are also connected to the CPU 201 via the bus 200, however, each of the display 102, the keyboard 103 and the mouse 104 may be connected directly to the CPU 201. In addition, the display 102 may be connected to the CPU 201 via a known graphic interface (not shown) which processes input and output image data.

In the computer system 100, the keyboard 103 and/or the mouse 104 form an input part of the molecule design support apparatus. The display 102 displays a three-dimensional molecular structure on the screen 102a in the half vector format or the ball-and-stick format. The CPU 201 functions as a determining part or means for determining, based on the bond axis specified from the input part, the end (or side) that becomes the target of the coordinate modification with respect to at least the bond axis that is specified, a modifying part or means for making a modification to the molecular structure, including a rotation around the specified bond axis or expansion and contraction of the specified bond axis, based on the modification specified from the input part, and a display part or means for displaying the modified molecular structure on the screen 102a of the display 102.

The structure of the computer system 100 is of course not limited to the structure shown in FIGS. 5 and 6, and a computer system having any known suitable structure may be used in place of the computer system 100.

Figure 7:
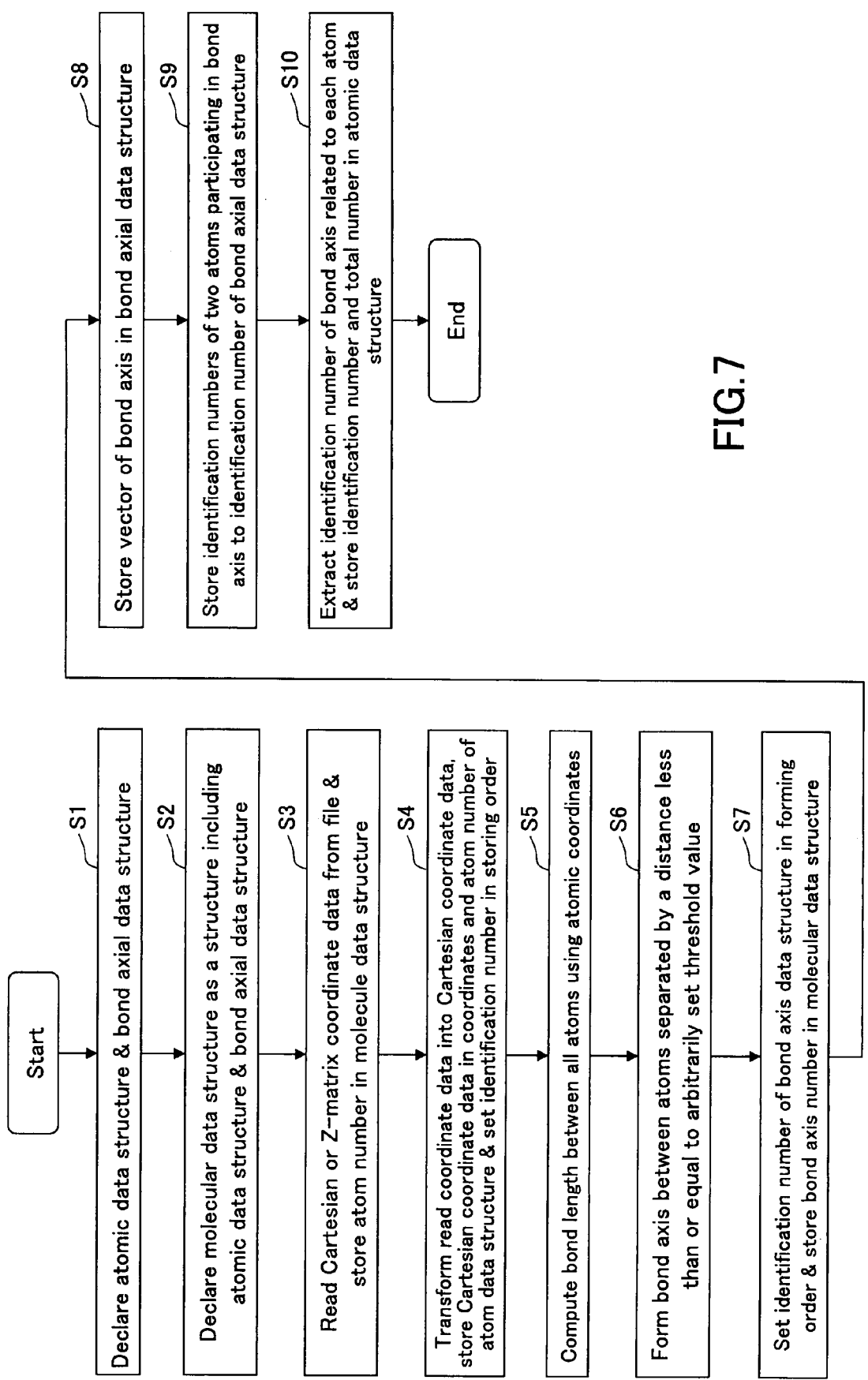
FIG. 7 is a flow chart for explaining a formation of an initial data structure.

FIG. 7 is a flow chart for explaining a formation of an initial data structure. The process shown in FIG. 7 is carried out by the CPU 201.

In FIG. 7, a step S1 declares an atomic data structure having the atom data structure A shown in FIG. 1, and a bond axial data structure having the bond axis data structure B shown in FIG. 1. A step S2 declares a molecular data structure having the molecule data structure M shown in FIG. 1, as a structure including the atomic data structure and the bond axial data structure. A step S3 reads Cartesian or Z-matrix coordinate data from a file within a storage part, and stores the atom number in the molecule data structure M. The storage part may be formed by the memory part 202, the disk drive 203 or the HDD 204 within the computer system 100 or, by the recording medium 106 or the like external to the computer system 100. A step S4 transforms the read coordinate data into the Cartesian coordinate data if the read coordinate data is the Z-matrix coordinate data, stores the Cartesian coordinate data in the coordinates and the atom number of the atom data structure A, and sets the identification number in the storing order. A step S5 computes the bond length between all of the atoms using atomic coordinates.

A step S6 forms a bond axis between the atoms that are separated by a distance less than or equal to an arbitrarily set threshold value. A step S7 sets the identification number of the bond axis data structure B in the forming order, and stores the bond axis number in the molecular data structure. A step S8 stores the vector of the bond axis in the bond axial data structure. A step S9 stores the identification numbers of the two atoms participating in the bond axis to the identification number of the bond axial data structure. A step S10 extracts the identification number of the bond axis related to each atom, and stores the identification number and the total number in the atomic data structure, and the process ends. Hence, with respect to the data of a given molecular structure, the initial data structure is formed from the atom data structure A, the bond axis data structure B and the molecule data structure M shown in FIG. 1.

(Free Rotation Around Atom)

Figure 8:
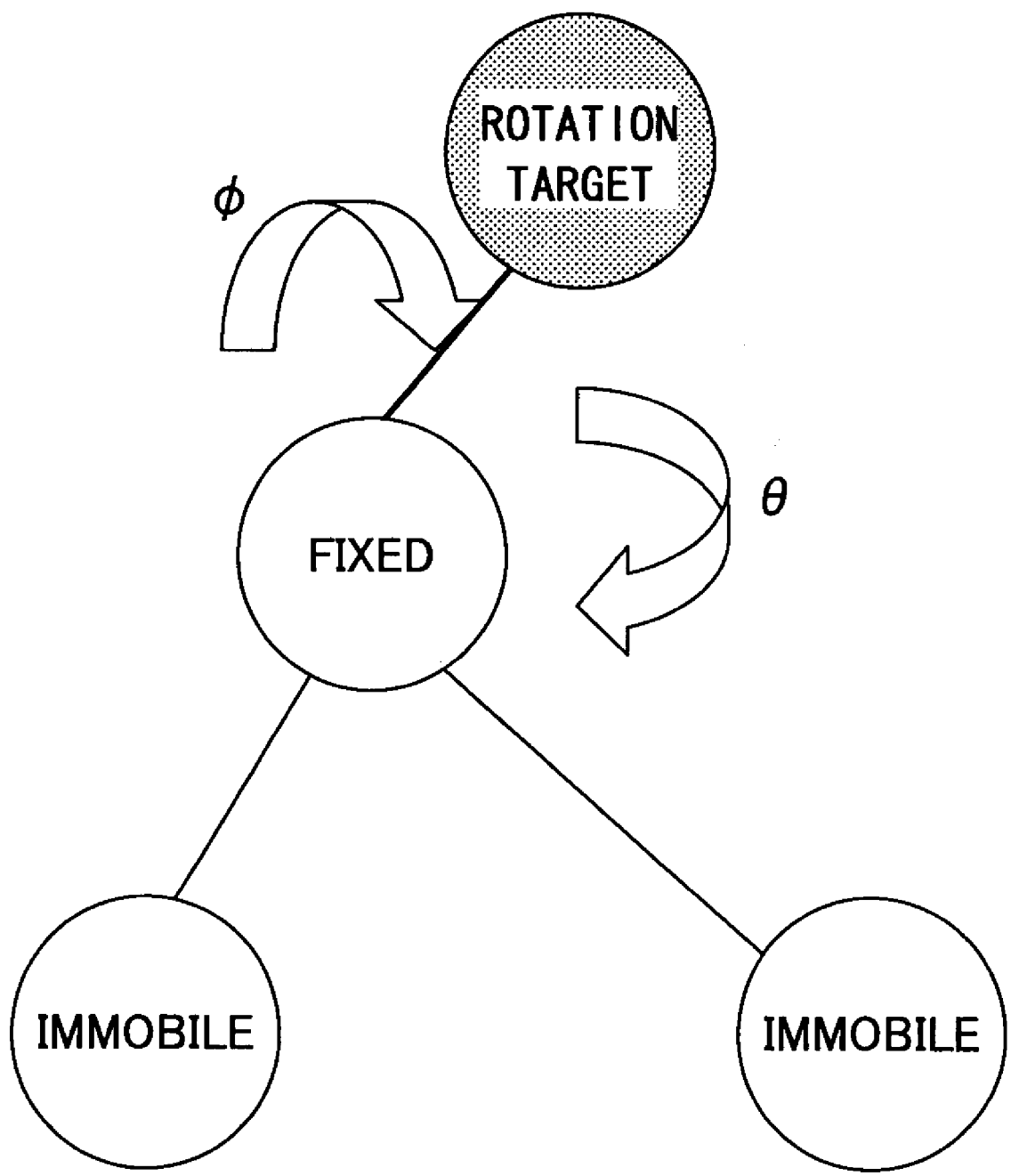
FIG. 8 is a diagram for explaining a rotation around a bond axis.

FIG. 8 is a diagram for explaining a rotation around a bond axis. FIG. 8 shows a state where the atom that is the rotation target is bonded to a fixed atom via a bond axis that is a rotary axis in this case, and this fixed atom is bonded to immobile atoms via bond axes.

With respect to the data structures shown in FIG. 1 prepared by the user by the process shown in FIG. 7, one item of the bond axis data structure B is selected. If it is assumed for the sake of convenience that the selected item is an identification number b1, a selection bit of the event flag belonging to the bond axis data having the identification number b1 is set. In this state, when the event information of the molecule data structure M is set to "free rotation around atom", a "free rotation around atom" bit is set in the event flag of the molecule data structure M, and the selection bit of the identification flag of all bond axis set data linked by bond axes other than the bond axis data having the identification number b1 is set, with respect to both terminal atoms (having identification numbers a1 and a2) of the bond axis data having the identification number b1. If the terminal atoms of the bond axis include the atom having the identification number a1 or a2, it is determined that the bond axis data having the identification number b1 belongs to the inside of a ring structure. In this case, a ring bit of the identification flag belonging to the terminal atom data is set. With respect to the bond axis set belonging to the terminal atom data in which the ring bit is set, the selection bit of the identification flag is cleared (or reset) so as to exclude the bond axis set from the target of the rotation operation. If the ring bit is not set, the number of selection bits of the bond axes linked from the atom having the identification number a1 and the number of selection bits of the bond axes linked from the atom having the identification number a2 are compared, and the smaller number of selection bits is maintained while the larger number of selection bits is cleared (or reset). Thereafter, the bond axis having the selection bit is represented as the rotation target. In addition, the bond axes having the selected identification number b1 is also included in the rotation target.

If not only the bond axis but one of the terminal atoms is also selected, the operation described above is carried out only with respect to the bond axis set linked to the selected atom or the atom that is not selected.

The three-dimensional rotation array around the atom or the quatemion is computed by making a drag-and-drop by the pointing device on the displayed molecular structure or, is determined by making a drag-and-drop in a command area other than a molecule display area in the main window or by setting the angle from the keyboard, and the process moves to the rotation operation. When the three-dimensional rotation array around the atom or the quatemion is specified by the drag-and-drop, the rotation operation is continuously carried during the dragging.

The rotation operation sets the "free rotation around atom" bit to the event flag of the bond axis data having the specified identification number b1, and makes the three-dimensional rotation array or the quatemion act on the bond axis that is the rotation target. Thereafter, the vector information of the bond axis is traced from one appropriate atom so as to reform the Cartesian coordinates of the atom data structure A, and the modified molecular structure is displayed in the main window.

Figure 9:
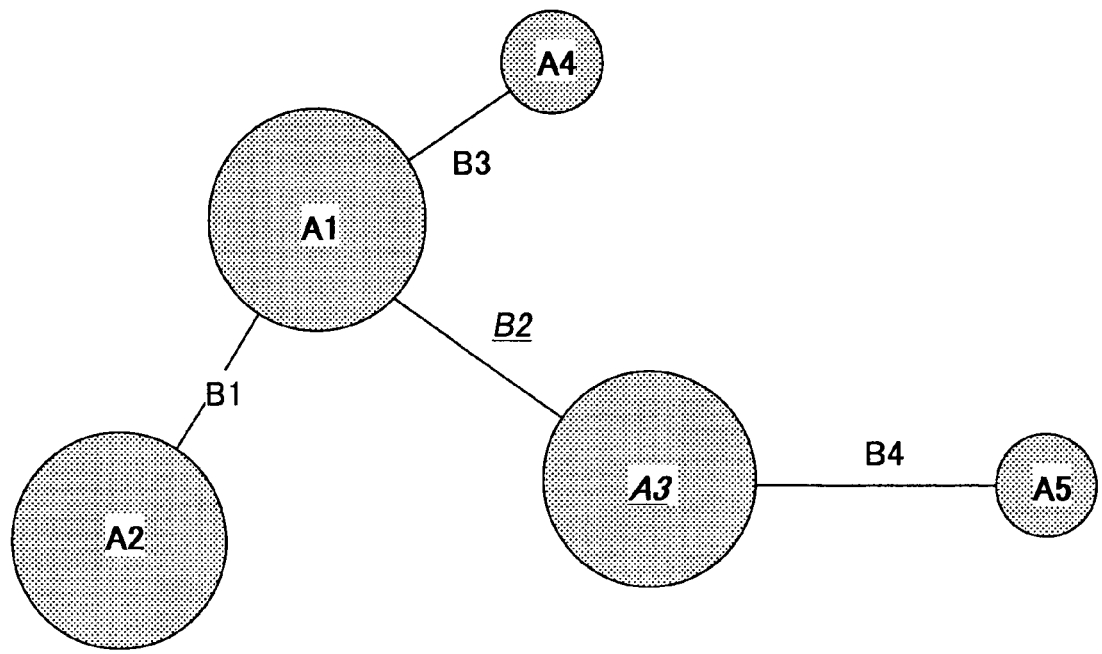
FIG. 9 is a diagram for explaining a free rotation around an atom by taking formic acid (HCOOH) as an example.
Figure 10:
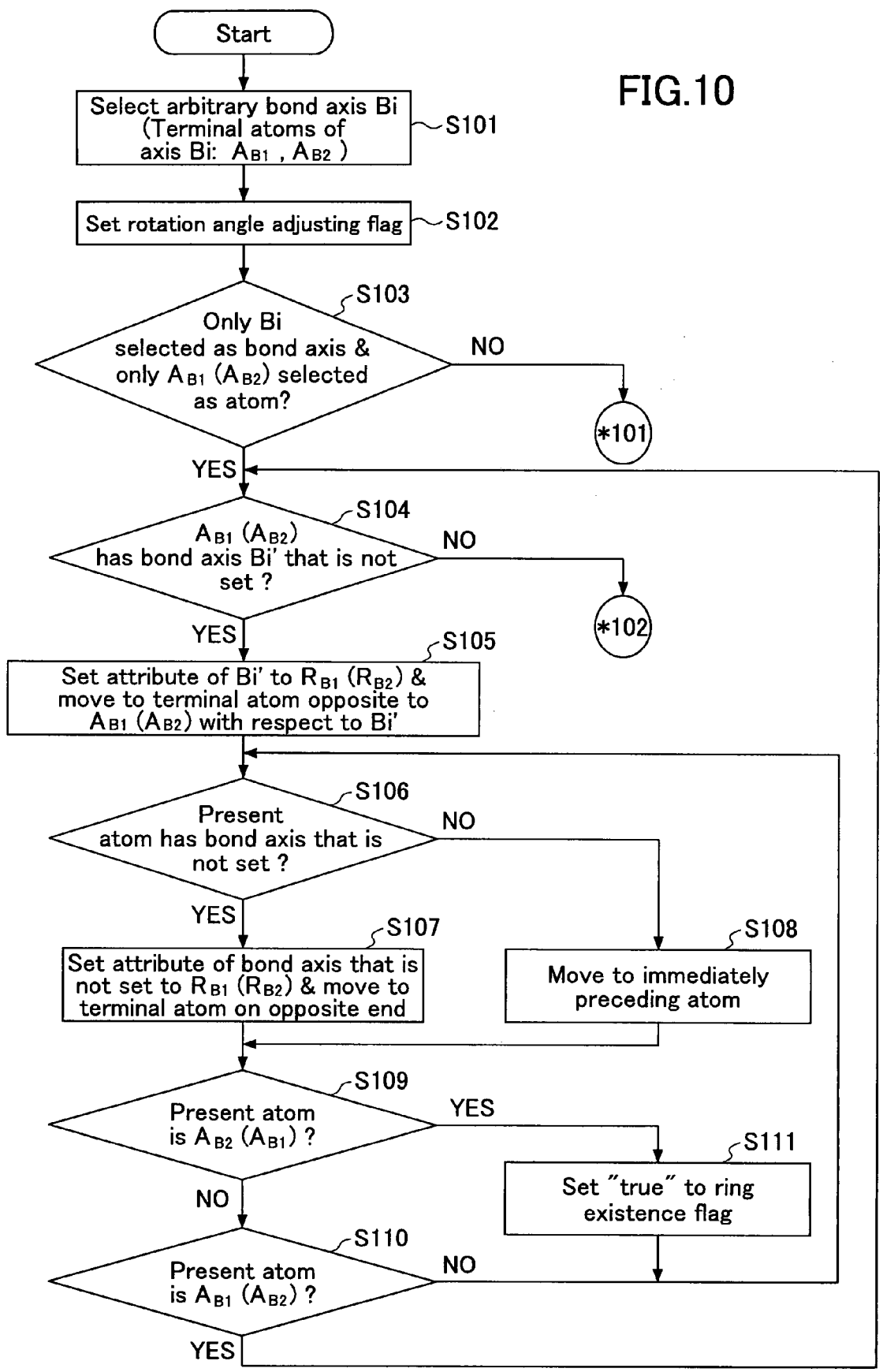
FIG. 10 is a flow chart for explaining the free rotation around the atom.
Figure 11:
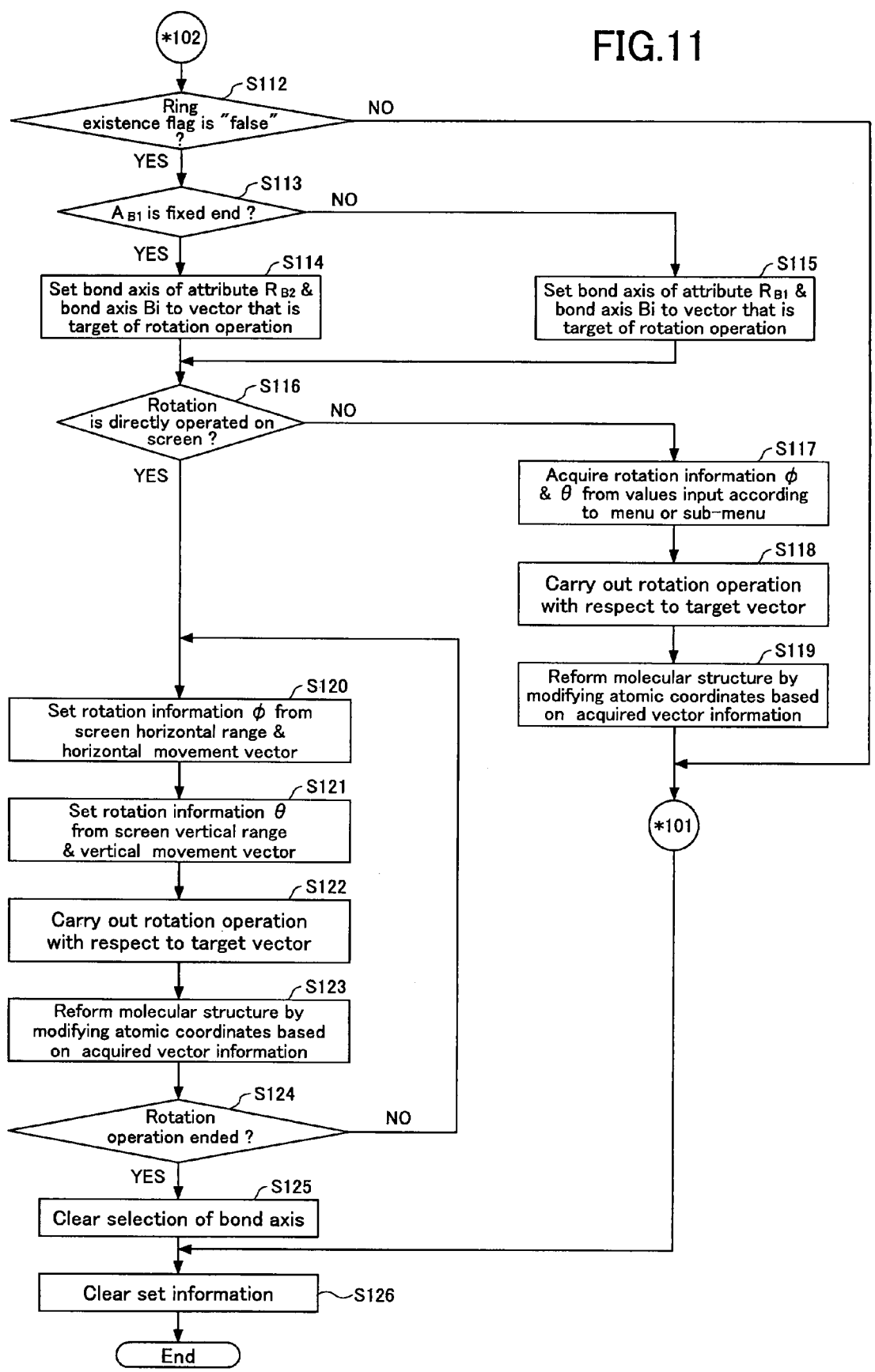
FIG. 11 is a flow chart for explaining the free rotation around the atom.
Figure 12:
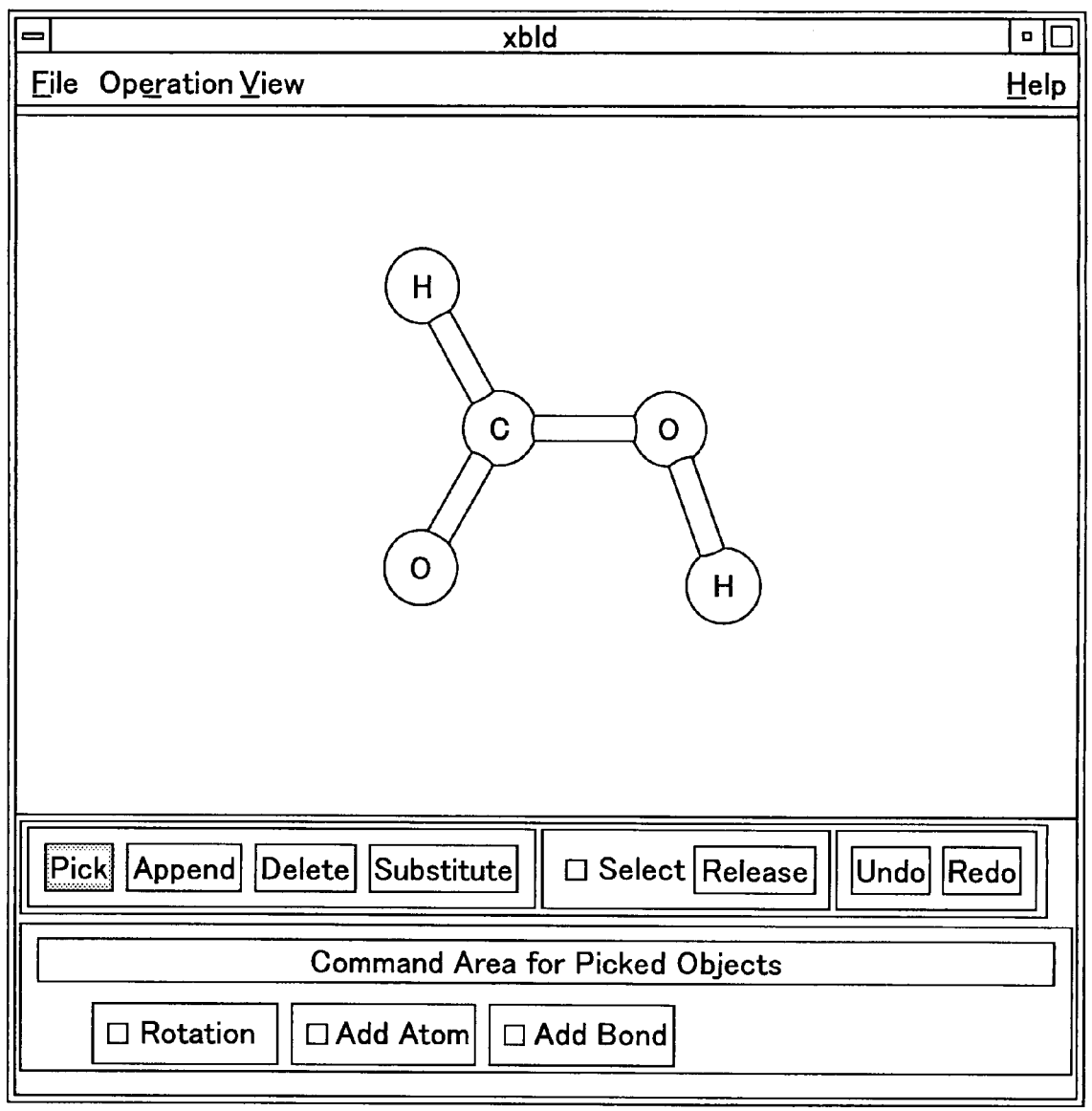
FIG. 12 is a diagram showing a display screen when making a free rotation operation around the atom.
Figure 13:
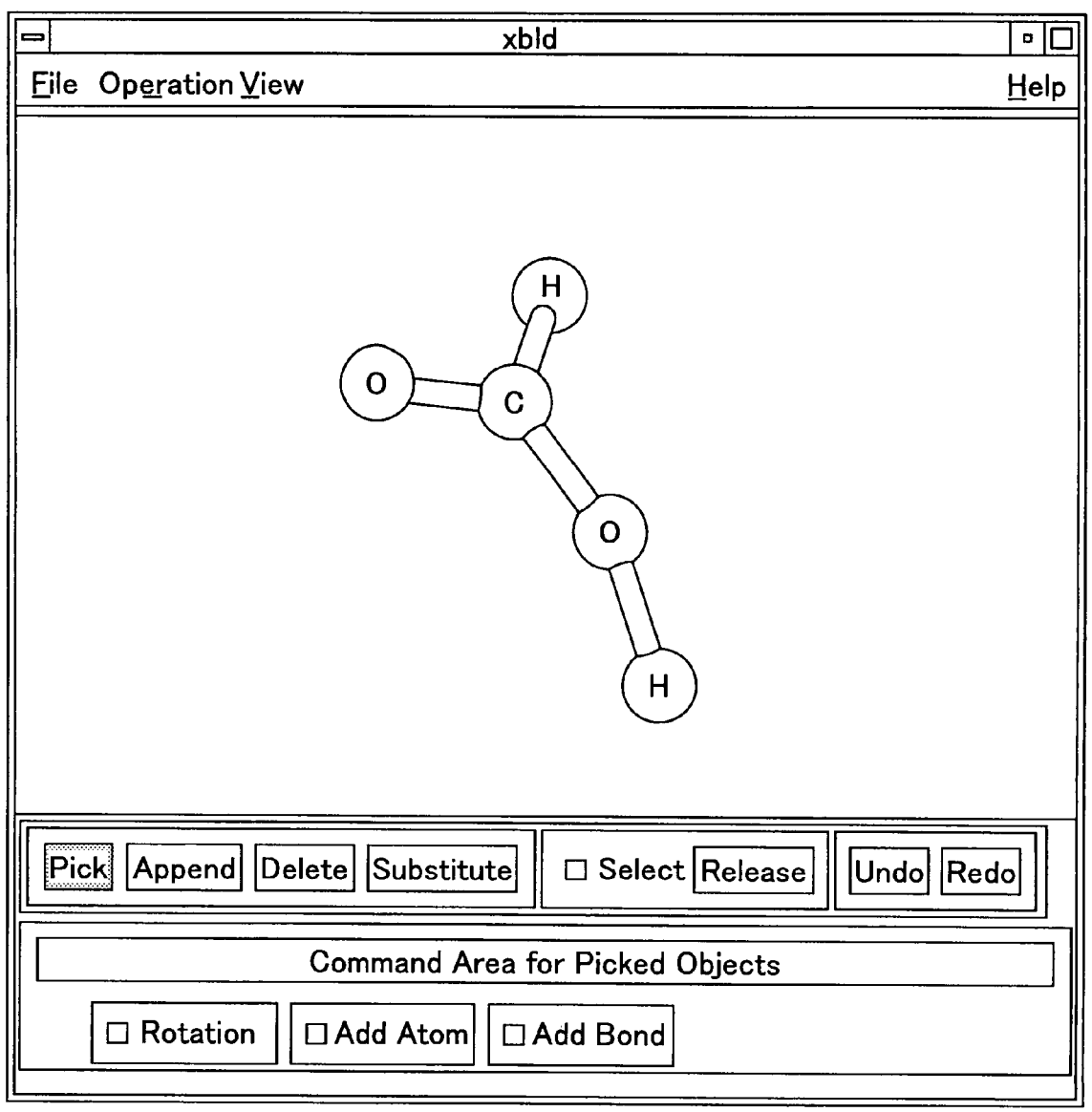
FIG. 13 is a diagram showing a display screen when making the free rotation operation around the atom.

FIG. 9 is a diagram for explaining the free rotation around the atom by taking formic acid (HCOOH) as an example. FIGS. 10 and 11 are flow charts for explaining the free rotation around the atom, and FIGS. 12 and 13 are diagrams showing a display screen when making the free rotation operation around the atom. FIG. 10 shows the process from the operation of selecting the bond axis item (also the atom item if necessary) up to the setting of a ring existence flag, and FIG. 11 shows the process from the setting of the rotation target and the rotation computation up to the actual modification of the structure.

In FIG. 10, a step S101 selects an arbitrary bond axis Bi. It is assumed for the sake of convenience that terminal atoms of the bond axis Bi are $A_{B1}$ and $A_{B2}$. A step S102 sets a rotation angle adjusting flag, that is, sets the "rotation around bond axis" bit to the event information flag of the molecular data. A step S103 judges whether or not only the bond axis Bi is selected as the bond axis and only the terminal atom $A_{B1}$ (or $A_{B2}$) is selected. If the judgement result in the step S103 is NO, the process advances to a step S126 shown in FIG. 11 which will be described later. On the other hand, if the judgement result in the step S103 is YES, a step S104 judges whether or not the terminal atom $A_{B1}$ (or $A_{B2}$) has a bond axis Bi' that is not yet set. If the judgement result in the step S104 is NO, the process advances to a step S112 shown in FIG. 11 which will be described later.

If the judgement result in the step S104 is YES, a step S105 sets the attribute of the bond axis Bi' to $R_{B1}$ (or $R_{B2}$), and moves to the terminal atom opposite to the terminal atom $A_{B1}$ (or $A_{B2}$) with respect to the bond axis Bi'. A step S106 judges whether or not the present atom has a bond axis that has not yet been set. If the judgement result in the step S106 is YES, a step S107 sets the attribute of the bond axis that is not yet set to $R_{B1}$ (or $R_{B2}$), and moves to the terminal atom on the opposite end. If the judgement result in the step S106 is NO, a step S108 moves to the immediately preceding atom, that is, the atom on the opposite end of the bond axis that is set. After the step S107 or S108, a step S109 judges whether or not the present atom is $A_{B2}$ (or $A_{B1}$) If the judgement result in the step S109 is NO, a step S110 judges whether or not the present atom is $A_{B1}$ (or $A_{B2}$) On the other hand, if the judgement result in the step S109 is YES, a step S111 sets "true" to the ring existence flag (sets the ring bit of the identification flag). If the judgement result in the step S110 is YES, the process returns to the step S104. If the judgement result in the step S110 is NO or, after the step S111, the process returns to the step S106.

In FIG. 11, the step S112 judges whether or not the ring existence flag is "false" (the ring bit of the identification flag is not set). If the judgement result in the step S112 is NO, the process advances to the step S126 which will be described later. If the judgement result in the step S112 is YES, a step S113 judges whether or not the atom $A_{B1}$ is a fixed end. If the judgement result in the step S113 is YES, a step S114 sets the bond axis of the attribute $R_{B2}$ and the bond axis Bi to the vector that is the target of the rotation operation, and the process advances to a step S116. On the other hand, if the judgement result in the step S113 is NO, a step S115 sets the bond axis of the attribute $R_{B1}$ and the bond axis Bi to the vector that is the target of the rotation operation, and the process advances to the step S116.

The step S116 judges whether or not the rotation is directly operated on the screen 102a. If the judgement result in the step S116 is NO, a step S117 acquires rotation information $\phi$ and $\theta$ from the values input from the input part according to a menu or sub-menu on the screen 102a. A step S118 carries out a rotation operation with respect to the target vector based on the rotation information $\phi$ and $\theta$, and a step S119 reforms the molecular structure by modifying the atomic coordinates based on the acquired vector information. After the step S119, the process advances to the step S126 which will be described later.

On the other hand, if the judgement result in the step S116 is YES, a step S120 sets the rotation information $\phi$ from the screen horizontal range and the horizontal movement vector on the screen 102a caused by the drag-and-drop of the mouse 104, and a step S121 sets the rotation information $\theta$ from the screen vertical range and the vertical movement vector on the screen 102a caused by the drag-and-drop of the mouse 104. A step S122 carries out a rotation operation with respect to the target vector based on the rotation information $\phi$ and $\theta$, and a step S123 reforms the molecular structure by modifying the atomic coordinates based on the acquired vector information. A step S124 judges whether or not the rotation operation has ended, and the process returns to the step S120 if the judgement result in the step S124 is NO. If the judgement result in the step S124 is YES, a step S125 clears (or resets) the selection of the bond axis that is the rotation operation target. In addition, the step S126 clears (or resets) the set information, and the process ends.

Accordingly, first, the bond axis B2 shown in FIG. 9 is selected. When the rotation angle adjusting flag is set (the "free rotation around atom" bit is set to the event information flag of the molecular data) after this selection, a bond axis set (or group) $R_{A1}$ (B1, B3) linked to the bond axes not including the bond axis B2 is selected using the terminal atom A1 as the base point according to a recursive process (algorithm) in the second half of the process shown in FIG. 10, and a check is made to determine whether or not the ring existence flag is to be set to "true" (whether or not to set the ring bit of the identification flag belonging to a terminal atom A3 with respect to the bond axis set $R_{A1}$). In this case, the bond axis set having the ring existence flag that is "true" is excluded from the rotation operation target (the selection bit of the identification flag is cleared). If the ring existence flag of the bond axis set $R_{A1}$ is "true", the rotation operation target no longer exists, and thus, the set information is cleared and the rotation operation is ended.

On the other hand, if the ring existence flag of the bond axis set $R_{A1}$ is "false", the bond axis set having the large bond axis number is excluded from the rotation operation target (the selection bit of the identification flag is cleared). By these operations, the three-dimensional molecular structure that is displayed in the main window on the screen 102a of the display 102 becomes as shown in FIG. 12. Because the formic acid (HCOOH) shown in FIG. 12 does not have a ring structure, the rotation operation is possible in this state. Since the bond axis set $R_{A3}$ has the smaller bond axis number, only the selection bit of the bond axis B3 is set.

If the rotation operation becomes possible by the processes described above, the selection bit is set to the bond axes B1, B2 and B3 included in the bond axis set $R_{A3}$, so as to set the bond axes B1, B2 and B3 as the rotation targets, by the first half of the process (algorithm) shown in FIG. 11. This embodiment uses an algorithm that determines the rotation array by aligning the mouse cursor to the molecule that is displayed in the main window and comparing the direction and the length of the drag-and-drop with the size of the screen 102a. When the rotation array is determined, the bond axes B1, B2 and B3 are subjected to a rotation computation (or operation) by the second half of the process (algorithm) shown in FIG. 11 and respectively become bond axes B'1, B'2 and B'3, and the Cartesian coordinates of the atoms A1, A2 and A4 are modified to A'1, A'2 and A'4 by adding the vector from the atom A3, so as to modify the molecular structure in the main window. When the mouse 104 is released, it is regarded that the rotation has ended, and the rotation operation is ended by clearing the selection information and the set information. By these operations, the three-dimensional molecular structure displayed in the main window on the screen 102a of the display 102 becomes as shown in FIG. 13. FIG. 13 shows the result for a case where the drag-and-drop of the mouse 104 that determines the rotation array is made by moving the mouse 104 obliquely upwards towards the right.

In FIG. 9, it is assumed for the sake of convenience that B2 is the selected bond axis, the ring flag is "false", A1 is the atom at the fixed end, B1, B2 and B3 are the bond axes that are the rotation targets, and the rotation information is input by an operation on the screen. If the rotation computation is denoted by R, B'1=RB1, B'2=RB2 and B'3=RB3 stand, and the coordinate modification of A1, A2 and A4 are respectively represented by A'1=A3+B'2, A'2=A'1+B'1 and A'4=A'1+B'3.

(Rotation Around Bond Axis)

Figure 14:
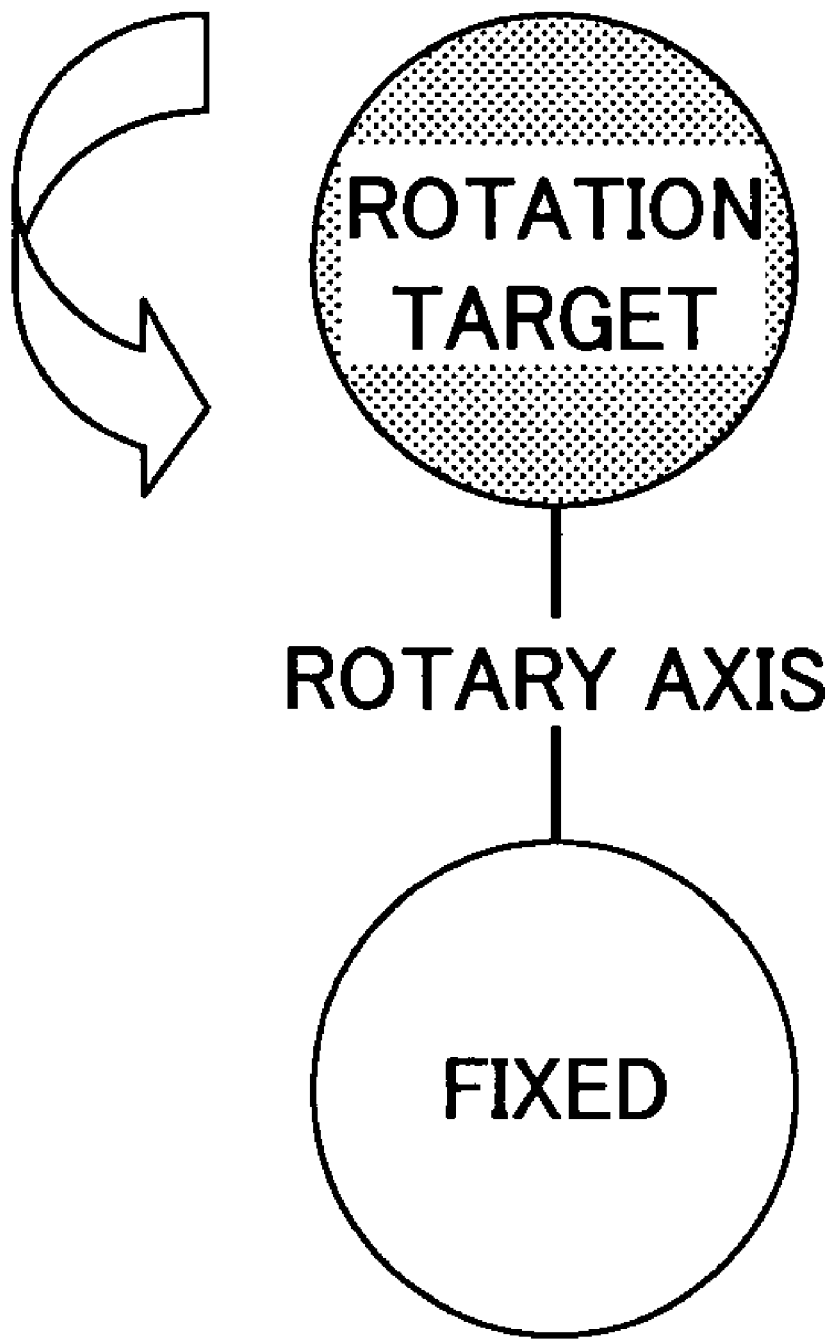
FIG. 14 is a diagram for explaining the rotation around the bond axis.

FIG. 14 is a diagram for explaining the rotation around the bond axis. FIG. 14 shows a state where the atom that is the rotation target is bonded to a fixed atom via a bond axis that is a rotary axis.

With respect to the data structures shown in FIG. 1 prepared by the user by the process shown in FIG. 7, one item of the bond axis data structure B is selected. If it is assumed for the sake of convenience that the selected item is an identification number b1, a selection bit of the event flag belonging to the bond axis data having the identification number b1 is set. In this state, when the event information of the molecule data structure M is set to "rotation around bond axis", a "rotation around bond axis" bit is set in the event flag of the molecule data structure M, and the selection bit of the identification flag of all bond axis set data linked by bond axes other than the bond axis data having the identification number b1 is set, with respect to both terminal atoms (having identification numbers a1 and a2) of the bond axis data having the identification number b1. If the terminal atoms of the bond axis include the atom having the identification number a1 or a2, it is determined that the bond axis data having the identification number b1 belongs to the inside of a ring structure. In this case, a ring bit of the identification flag belonging to the terminal atom data is set. With respect to the bond axis set belonging to the terminal atom data in which the ring bit is set, the selection bit of the identification flag is cleared (or reset) so as to exclude the bond axis set from the target of the rotation operation. If the ring bit is not set, the number of selection bits of the bond axes linked from the atom having the identification number a1 and the number of selection bits of the bond axes linked from the atom having the identification number a2 are compared, and the smaller number of selection bits is maintained while the larger number of selection bits is cleared (or reset). Thereafter, the bond axis having the selection bit is represented as the rotation target.

If not only the bond axis but one of the terminal atoms is also selected, the operation described above is carried out only with respect to the bond axis set linked to the selected atom or the atom that is not selected.

The rotation angle around the bond axis is computed by making a drag-and-drop by the pointing device on the displayed molecular structure or, is determined by making a drag-and-drop in a command area other than a molecule display area in the main window or by setting the angle from the keyboard, and the process moves to the rotation operation. When the rotation angle around the bond axis is specified by the drag-and-drop, the rotation operation is continuously carried during the dragging.

The rotation operation sets the "rotation around bond axis" bit to the event flag of the bond axis data having the specified identification number b1, and sets to the rotary axis the direction of the rotation target from the fixed end. The rotation operation computes the rotation array or the quatemion from the rotary axis and the rotation angle, and makes the rotation array or the quatemion act on the bond axis that is the rotation target. Thereafter, the vector information of the bond axis is traced from one appropriate atom so as to reform the Cartesian coordinates of the atom data structure A, and the modified molecular structure is displayed in the main window.

Figure 15:
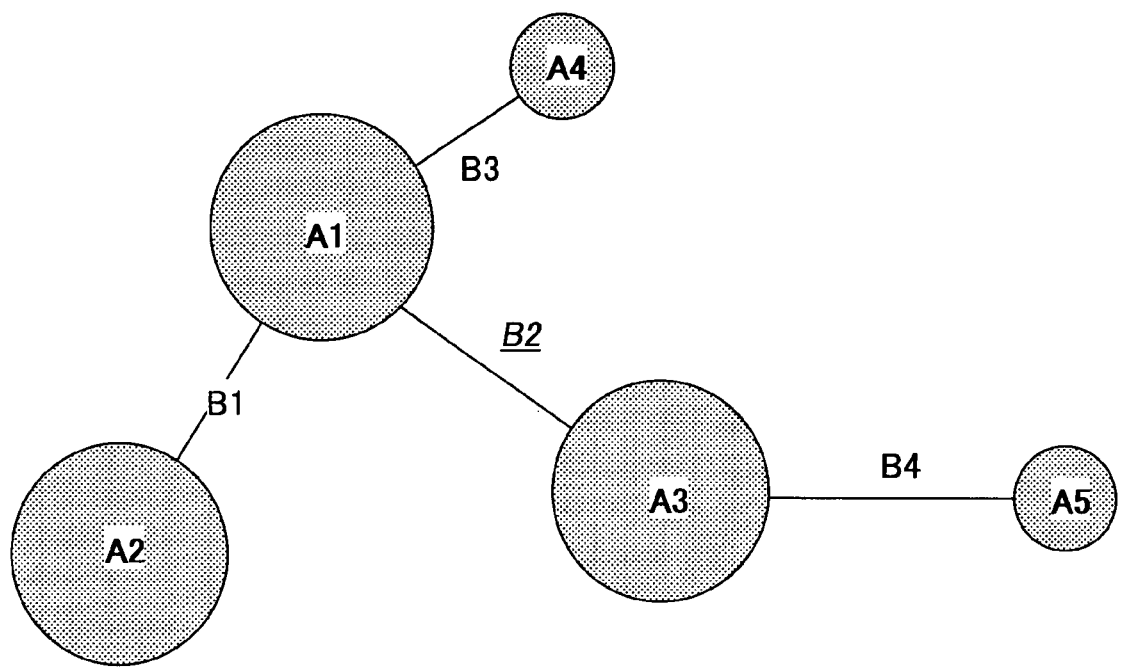
FIG. 15 is a diagram for explaining the rotation around the bond axis by taking formic acid (HCOOH) as an example.
Figure 16:
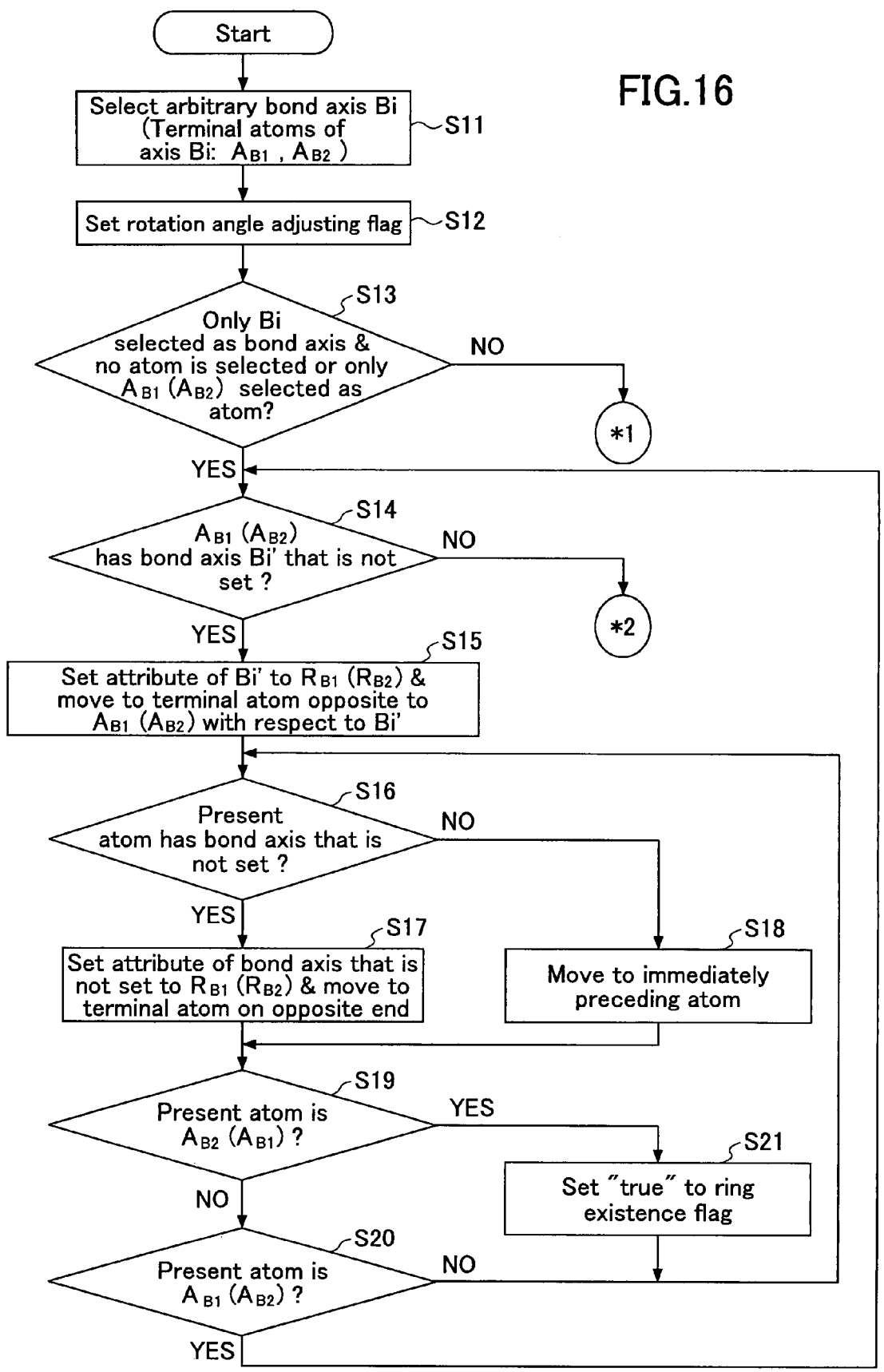
FIG. 16 is a flow chart for explaining the rotation around the bond axis.
Figure 17:
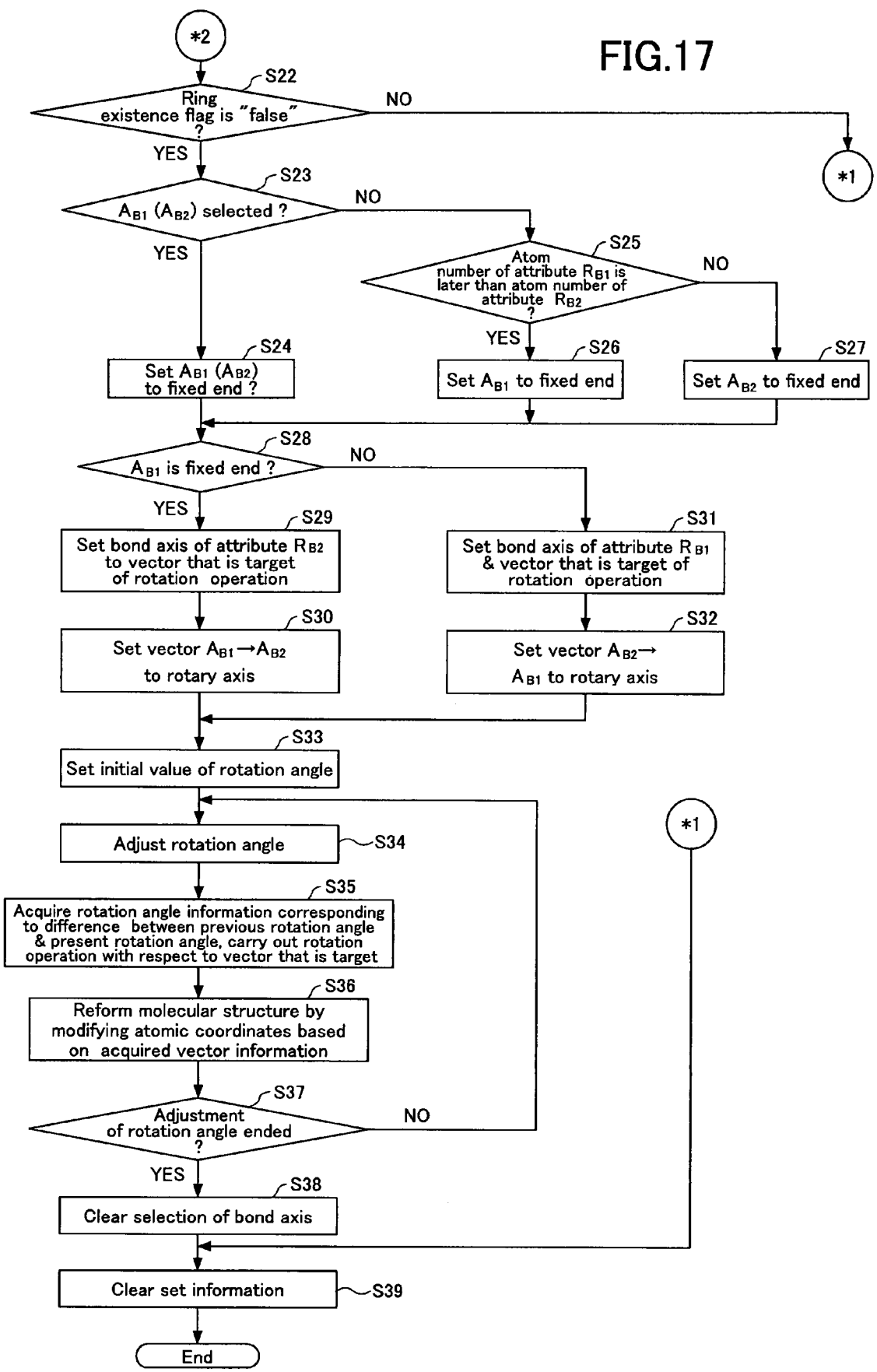
FIG. 17 is a flow chart for explaining the rotation around the bond axis.
Figure 18:
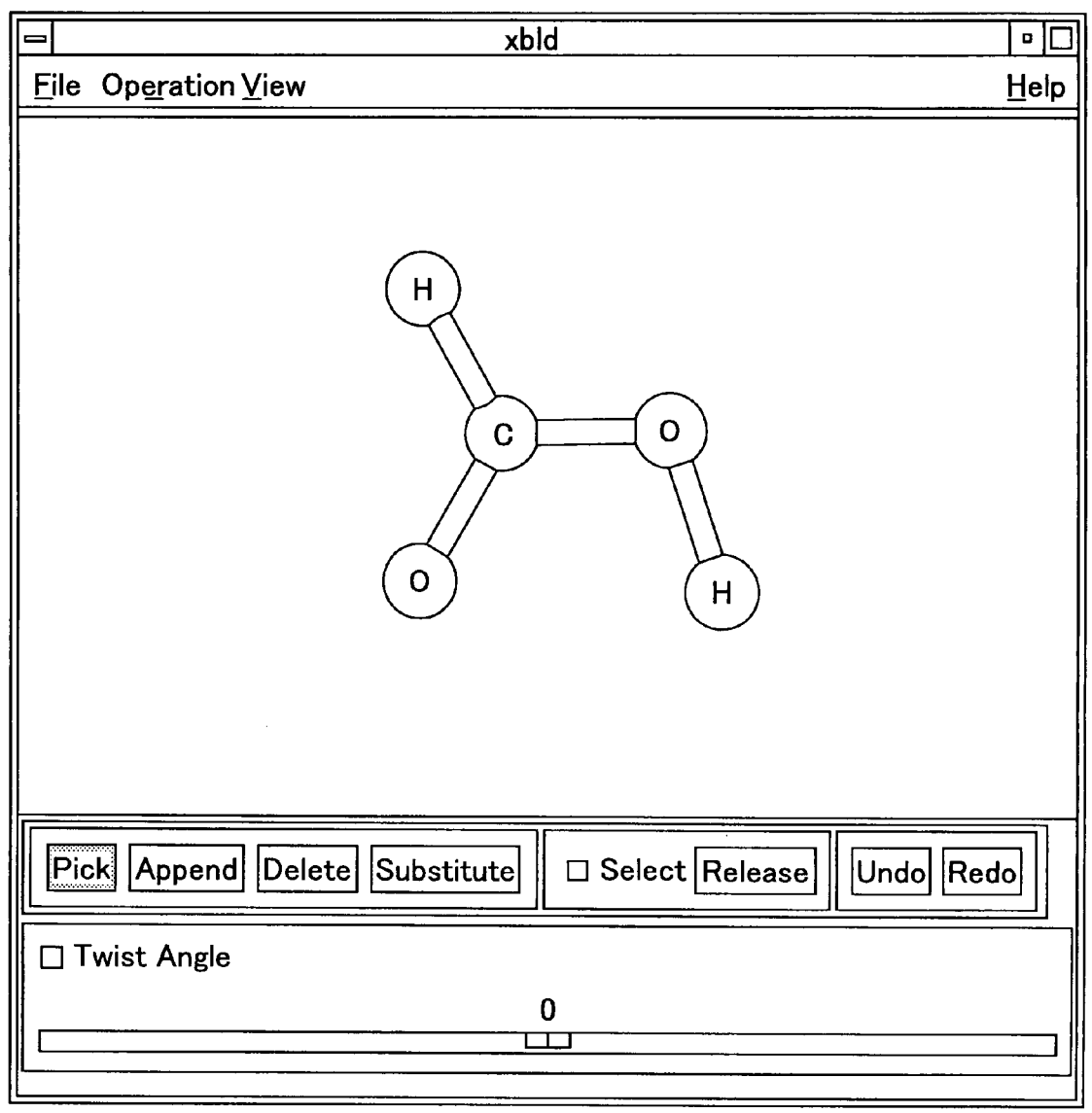
FIG. 18 is a diagram showing a display screen when making the rotation operation around the bond axis.
Figure 19:
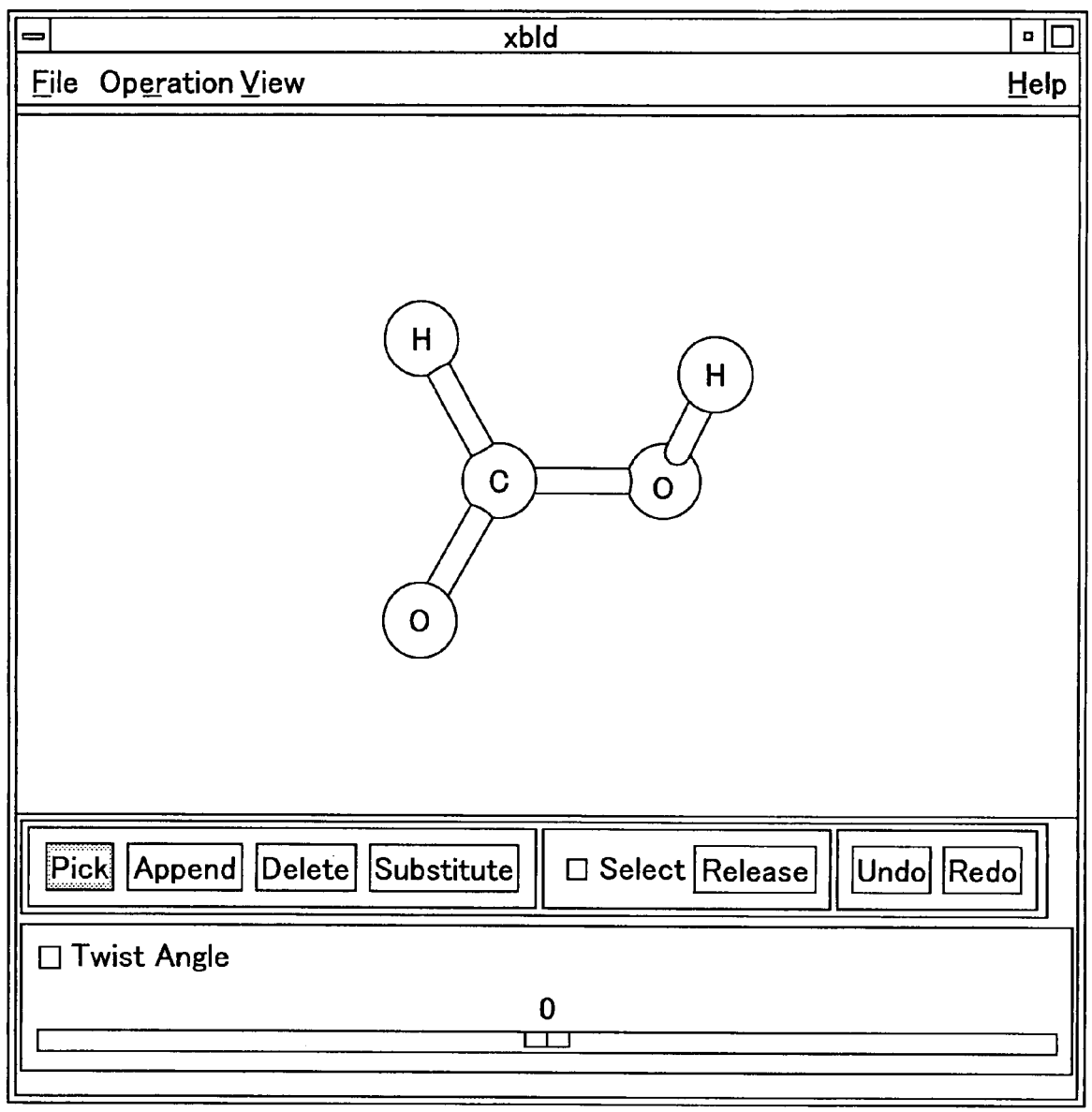
FIG. 19 is a diagram showing a display screen when making the rotation operation around the bond axis.

FIG. 15 is a diagram for explaining the rotation around the bond axis by taking the formic acid (HCOOH) as an example. FIGS. 16 and 17 are flow charts for explaining the rotation around the bond axis, and FIGS. 18 and 19 are diagrams showing a display screen when making the rotation operation around the bond axis. FIG. 16 shows the process from the operation of selecting the bond axis item (also the atom item if necessary) up to the setting of a ring existence flag, and FIG. 17 shows the process from the setting of the rotation target and the rotation computation up to the actual modification of the structure.

In FIG. 16, a step S11 selects an arbitrary bond axis Bi. It is assumed for the sake of convenience that terminal atoms of the bond axis Bi are $A_{B1}$ and $A_{B2}$. A step S12 sets a rotation angle adjusting flag, that is, sets the "rotation around bond axis" bit to the event information flag of the molecular data. A step S13 judges whether or not only the bond axis Bi is selected as the bond axis and no atom is selected or only the terminal atom $A_{B1}$ (or $A_{B2}$) is selected. If the judgement result in the step S13 is NO, the process advances to a step S39 shown in FIG. 17 which will be described later. On the other hand, if the judgement result in the step S13 is YES, a step S14 judges whether or not the terminal atom $A_{B1}$ (or $A_{B2}$) has a bond axis Bi' that is not yet set. If the judgement result in the step S14 is NO, the process advances to a step S22 shown in FIG. 17 which will be described later.

If the judgement result in the step S14 is YES, a step S15 sets the attribute of the bond axis Bi' to $R_{B1}$ (or $R_{B2}$), and moves to the terminal atom opposite to the terminal atom $A_{B1}$ (or $A_{B2}$) with respect to the bond axis Bi'. A step S16 judges whether or not the present atom has a bond axis that has not yet been set. If the judgement result in the step S16 is YES, a step S17 sets the attribute of the bond axis that is not yet set to $R_{B1}$ (or $R_{B2}$), and moves to the terminal atom on the opposite end. If the judgement result in the step S16 is NO, a step S18 moves to the immediately preceding atom, that is, the atom on the opposite end of the bond axis that is set. After the step S17 or S18, a step S19 judges whether or not the present atom is $A_{B2}$ (or $A_{B1}$). If the judgement result in the step S19 is NO, a step S20 judges whether or not the present atom is $A_{B1}$ (or $A_{B2}$). On the other hand, if the judgement result in the step S19 is YES, a step S21 sets "true" to the ring existence flag (sets the ring bit of the identification flag). If the judgement result in the step S20 is YES, the process returns to the step S14. If the judgement result in the step S20 is NO or, after the step S21, the process returns to the step S16.

In FIG. 17, the step S22 judges whether or not the ring existence flag is "false" (the ring bit of the identification flag is not set). If the judgement result in the step S22 is NO, the process advances to the step S39 which will be described later. If the judgement result in the step S22 is YES, a step S23 judges whether or not the atom $A_{B1}$ (or $A_{B2}$) has been selected. If the judgement result in the step S23 is YES, a step S24 sets the atom $A_{B1}$ (or $A_{B2}$) to the fixed end. If the judgement result in the step S23 is NO, a step S25 judges whether or not the atom number of the attribute $R_{B1}$ is lager than the atom number of the attribute $R_{B2}$. If he judgement result in the step S25 is YES, a step S26 sets the atom $A_{B1}$ to the fixed end. If the judgement result in the step S25 is NO, a step S27 sets the atom $A_{B2}$ to the fixed end. After the step S24 or, the step S26 or, the step S27, the process advances to a step S28.

The step S28 judges whether or not the atom $A_{B1}$ is the fixed end. If the judgement result in the step S28 is YES, a step S29 sets the bond axis of the attribute $R_{B2}$ to the vector that is the target of the rotation operation, and a step S30 sets the vector $A_{B1} \rightarrow A_{B2}$ to the rotary axis. On the other hand, if the judgement result in the step S28 is NO, a step S31 sets the bond axis of the attribute $R_{B1}$ to the vector that is the target of the rotation operation, and a step S32 sets the vector $A_{B2} \rightarrow A_{B1}$ to the rotary axis. After the step S30 or S32, the process advances to a step S33.

The step S33 sets the initial value of the rotation angle around the bond axis. A step S34 adjusts the rotation angle. A step S35 acquires rotation angle information corresponding to a difference between the previous rotation angle and the present rotation angle, and carries out a rotation operation with respect to the vector that is the target (that is, the target vector). A step S36 reforms the molecular structure by modifying the atomic coordinates based on the acquired vector information. A step S37 judges whether or not the adjustment of the rotation angle has ended, and the process returns to the step S34 if the judgement result in the step S37 is NO. If the judgement result in the step S37 is YES, a step S38 clears (or resets) the selection of the bond axis that is the rotation operation target. In addition, the step S39 clears (or resets) the set information, and the process ends.

Accordingly, first, the bond axis B2 shown in FIG. 15 is selected. When the rotation angle adjusting flag is set (the "rotation around bond axis" bit is set to the event information flag of the molecular data) after this selection, a bond axis set (or group) $R_{A1}$ (B1, B3) linked to the bond axes not including the bond axis B2 is selected using the terminal atom A1 as the base point according to a recursive process (algorithm) in the second half of the process shown in FIG. 16, and a check is made to determine whether or not the ring existence flag is to be set to "true" (whether or not to set the ring bit of the identification flag belonging to a terminal atom A3 with respect to the bond axis set $R_{A1}$, and whether or not to set the ring bit of the identification flag belonging to the terminal atom A1 with respect to the bond axis set $R_{A3}$). In this case, the bond axis set having the ring existence flag that is "true" is excluded from the rotation operation target (the selection bit of the identification flag is cleared). If the ring existence flag of both the bond axis sets $R_{A1}$ and $R_{A3}$ is "true", the rotation operation target no longer exists, and thus, the set information is cleared and the rotation operation is ended.

On the other hand, if the ring existence flag of both the bond axis sets $R_{A1}$ and $R_{A3}$ is "false", the bond axis set having the large bond axis number is excluded from the rotation operation target (the selection bit of the identification flag is cleared). By these operations, the three-dimensional molecular structure that is displayed in the main window on the screen 102a of the display 102 becomes as shown in FIG. 18. Because the formic acid (HCOOH) shown in FIG. 18 does not have a ring structure, the rotation operation is possible in this state. Since the bond axis set $R_{A3}$ has the smaller bond axis number, only the selection bit of the bond axis B3 is set.

If the rotation operation becomes possible by the processes described above, the selection bit is set to the bond axis B4 included in the bond axis set $R_{A3}$, so as to set the bond axis B4 as the rotation target, by the first half of the process (algorithm) shown in FIG. 17. The rotary axis of the bond axis B4 is set to a vector having the direction A1→A3 in a direction of the bond axis B2. This embodiment uses an algorithm that determines the rotation array from the rotary axis and the rotation angle, by displaying a slide bar in the command window that is displayed in the main window, and determining the rotation angle by a drag-and-drop of the slide bar by the mouse 104. When the rotation array is determined, the bond axis B4 is subjected to a rotation computation (or operation) by the second half of the process (algorithm) shown in FIG. 17 and becomes bond axis B'4, and the Cartesian coordinates of the atom A5 are modified to A'5 by adding the vector from the atom A3, so as to modify the molecular structure in the main window. When the mouse 104 is released, it is regarded that the rotation has ended, and the rotation operation is ended by clearing the selection information and the set information. By these operations, the three-dimensional molecular structure displayed in the main window on the screen 102a of the display 102 becomes as shown in FIG. 19. FIG. 19 shows the result for a case where a rotation of −133 degrees around the bond axis is made by the drag-and-drop of the mouse 104.

In FIG. 15, it is assumed for the sake of convenience that B2 is the selected bond axis, the ring flag is "false", A1 is the atom at the fixed end, B4 is the bond axis that is the rotation target, and A1→A3 is the rotary axis. If the rotation computation is denoted by R, B'4=RB4 stands, and the coordinate modification of A5 is represented by A'5=A3+B'4.

(Angle Modification Between Two Axes)

Figure 20:
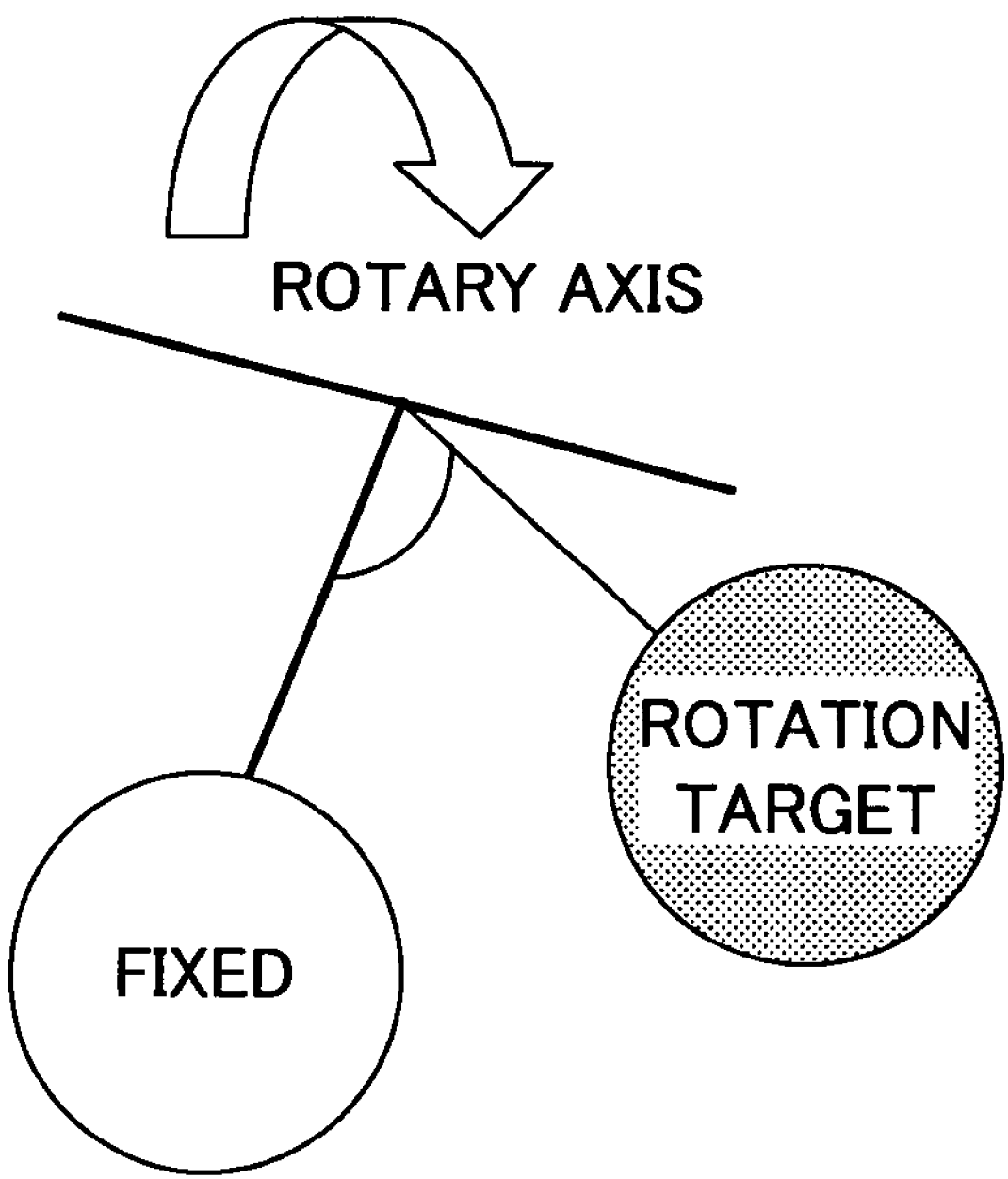
FIG. 20 is a diagram for explaining an angle modification between two axes.

FIG. 20 is a diagram for explaining an angle modification between two axes. FIG. 20 shows a state where the atom that is the rotation target is bonded to a fixed atom via a bond axis that is a rotary axis and still another bond axis.

With respect to the data structures shown in FIG. 1 prepared by the user by the process shown in FIG. 7, two items of the bond axis data structure B are selected. If it is assumed for the sake of convenience that the selected items are identification numbers b1 and b2, a selection bit of the event flag belonging to the bond axis data having the identification numbers b1 and b2 is set. In this state, when the event information of the molecule data structure M is set to "angle modification between two axes", a "angle modification between two axes" bit is set in the event flag of the molecule data structure M, by regarding the bond axis data to be continuous (linked) only when the atomic data of one of the terminal atoms belonging to the bond axis data having the identification number b1 includes the bond axis having the identification number b2. The selection bit of the identification flag of all bond axis set data linked by bond axes other than the bond axis data having the identification numbers ab1 to b1 and the identification numbers ab2 to b2 is set, with respect to both terminal atoms (having identification numbers ab1 and ab2) of the bond axis data having the identification numbers b1 and b2. If the terminal atoms of the bond axis include the atom having the identification number ab2 or ab1, it is determined that the bond axis data having the identification numbers b1 and b2 belong to the inside of a ring structure. In this case, a ring bit of the identification flag belonging to the terminal atom data is set. With respect to the bond axis set belonging to the terminal atom data in which the ring bit is set, the selection bit of the identification flag is cleared (or reset) so as to exclude the bond axis set from the target of the rotation operation. If the ring bit is not set, the number of selection bits of the bond axes linked from the atom having the identification number ab1 and the number of selection bits of the bond axes linked from the atom having the identification number ab2 are compared, and the smaller number of selection bits is maintained while the larger number of selection bits is cleared (or reset). Thereafter, the bond axis having the selection bit is represented as the rotation target.

If not only the two continuous bond axes but one of the terminal atoms is also selected, the operation described above is carried out only with respect to the bond axis set linked to the selected atom or the atom that is not selected.

The angle between two axes is computed by making a drag-and-drop by the pointing device on the displayed molecular structure or, is determined by making a drag-and-drop in a command area other than a molecule display area in the main window or by setting the angle from the keyboard, and the process moves to the rotation operation. When the angle between two axes is specified by the drag-and-drop, the rotation operation is continuously carried during the dragging.

The rotation operation sets the "angle modification between two axes" bit to the event flag of the bond axis data having the specified identification numbers b1 and b2, and sets to the rotary axis a vector that is perpendicular to both the bond axes having the identification numbers b1 and b2. The rotation operation computes the rotation array or the quatemion from the rotary axis and the rotation angle, and makes the rotation array or the quatemion act on the bond axis that is the rotation target. Thereafter, the vector information of the bond axis is traced from one appropriate atom so as to reform the Cartesian coordinates of the atom data structure A, and the modified molecular structure is displayed in the main window.

Figure 21:
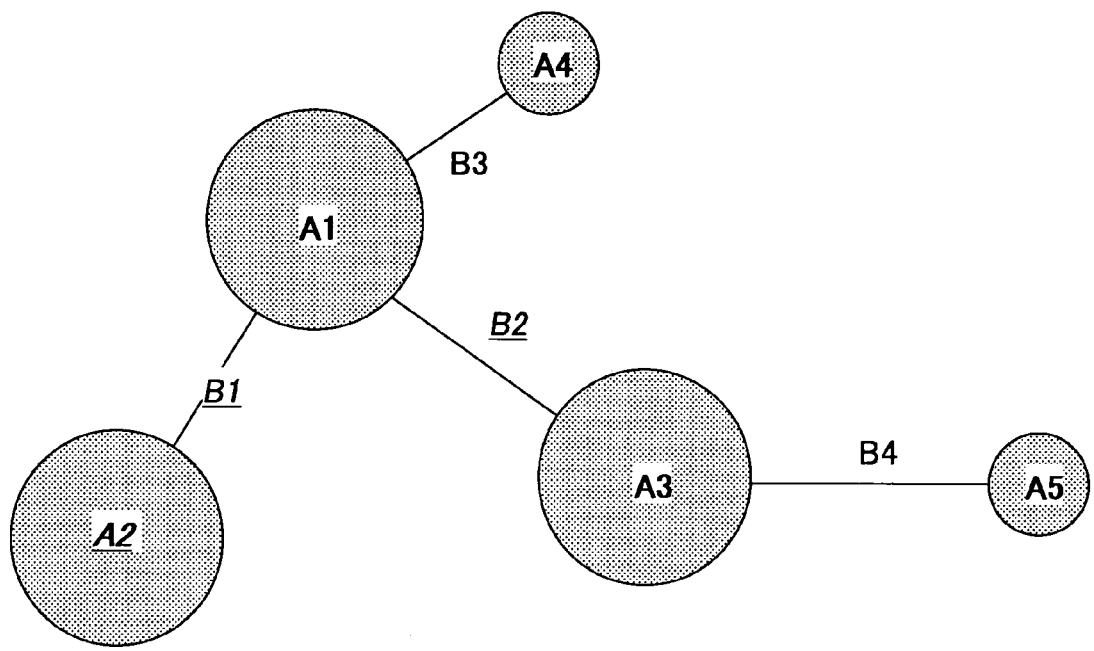
FIG. 21 is a diagram for explaining the angle modification between two axes by taking formic acid (HCOOH) as an example.
Figure 22:
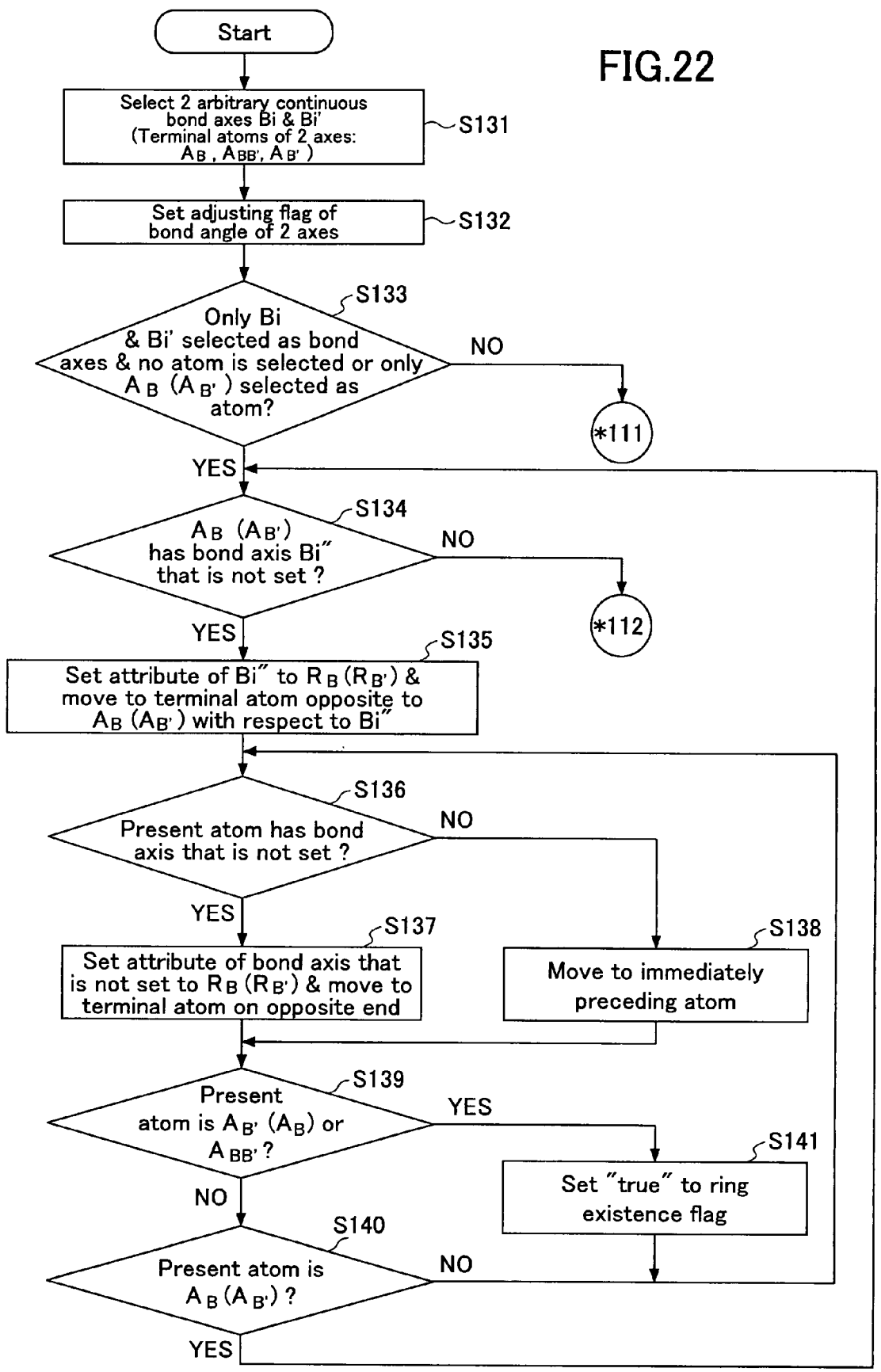
FIG. 22 is a flow chart for explaining the angle modification between two axes.
Figure 23:
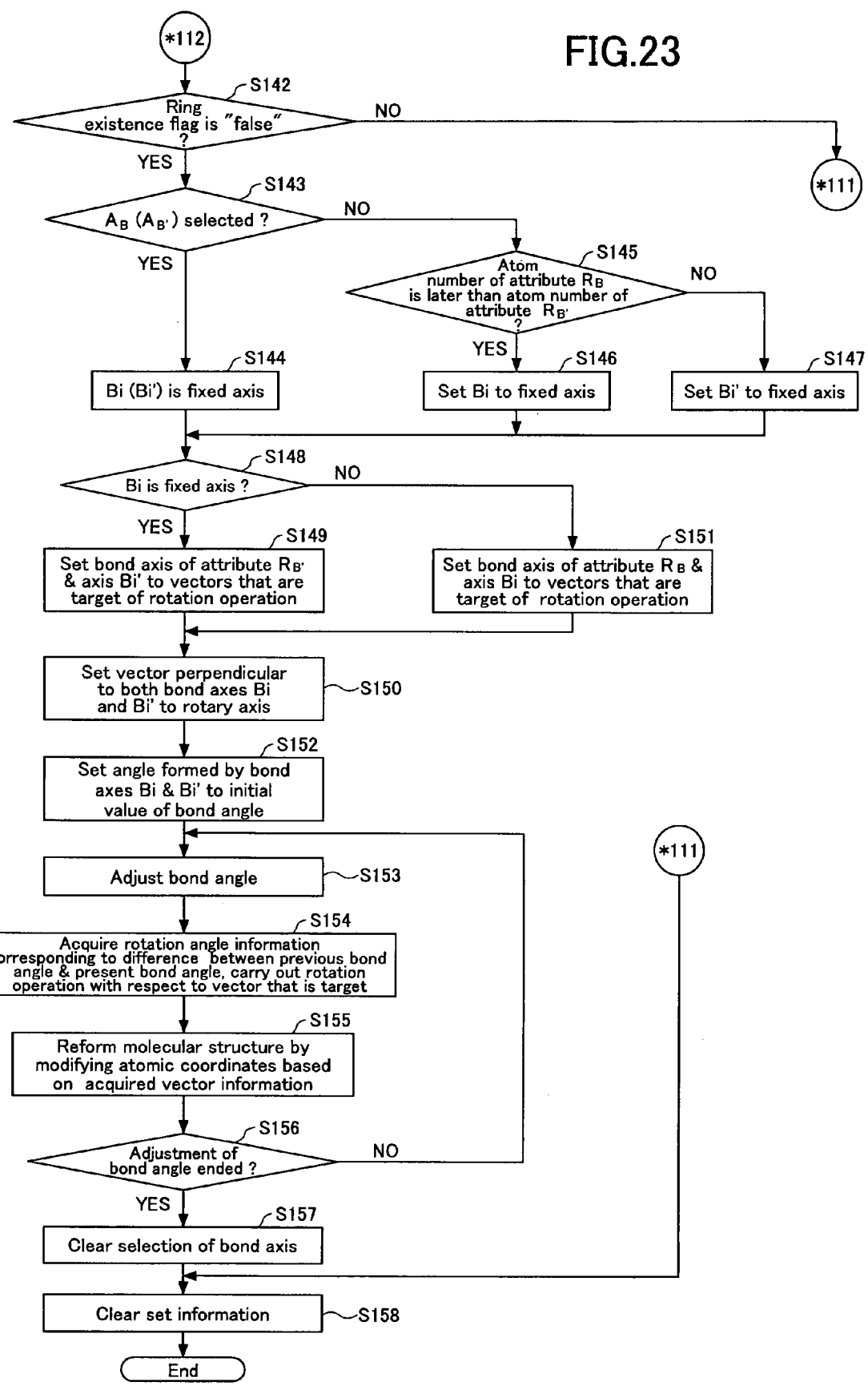
FIG. 23 is a flow chart for explaining the angle modification between two axes.
Figure 24:
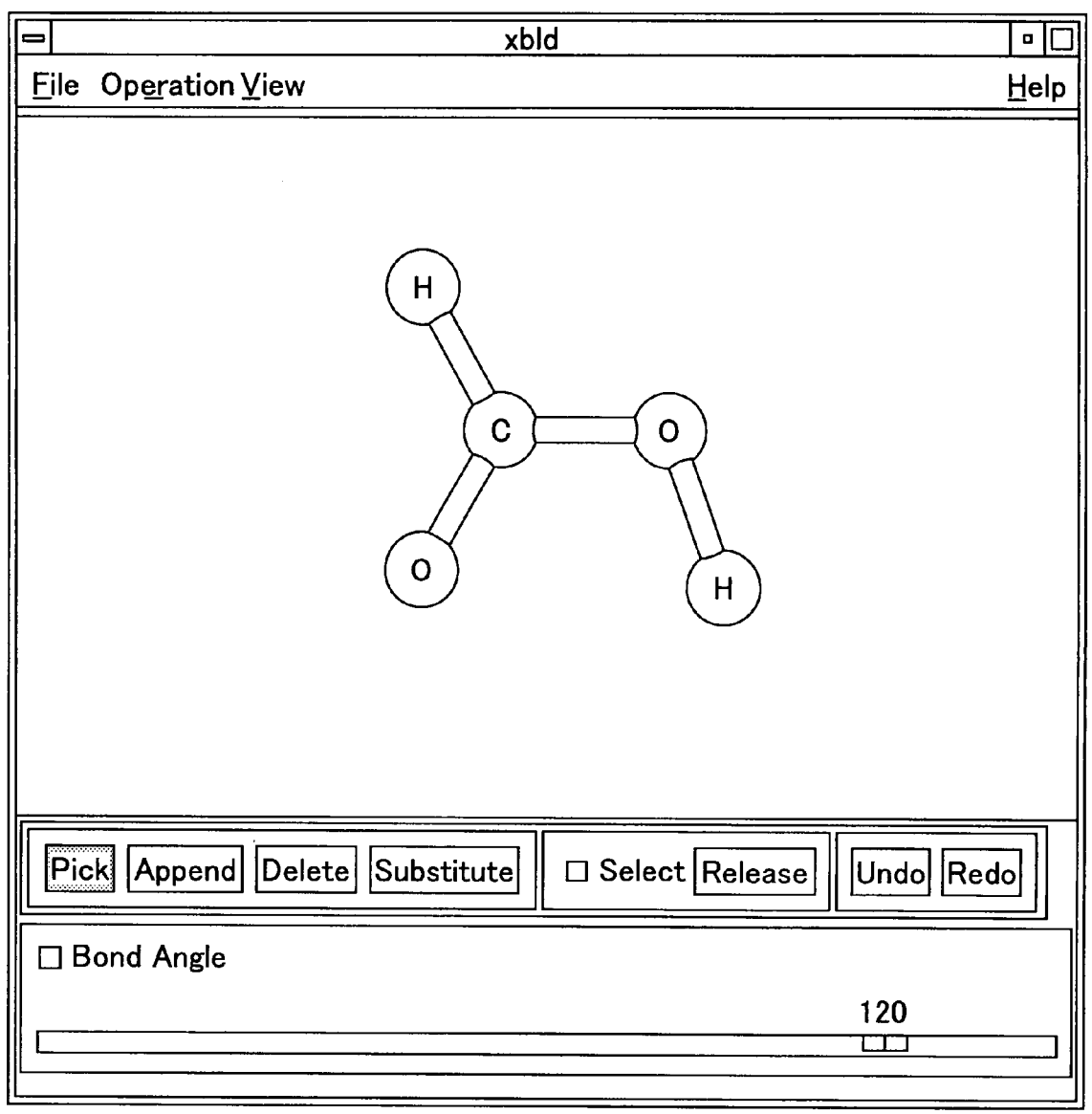
FIG. 24 is a diagram showing a display screen when making an angle modifying operation between two axes.
Figure 25:
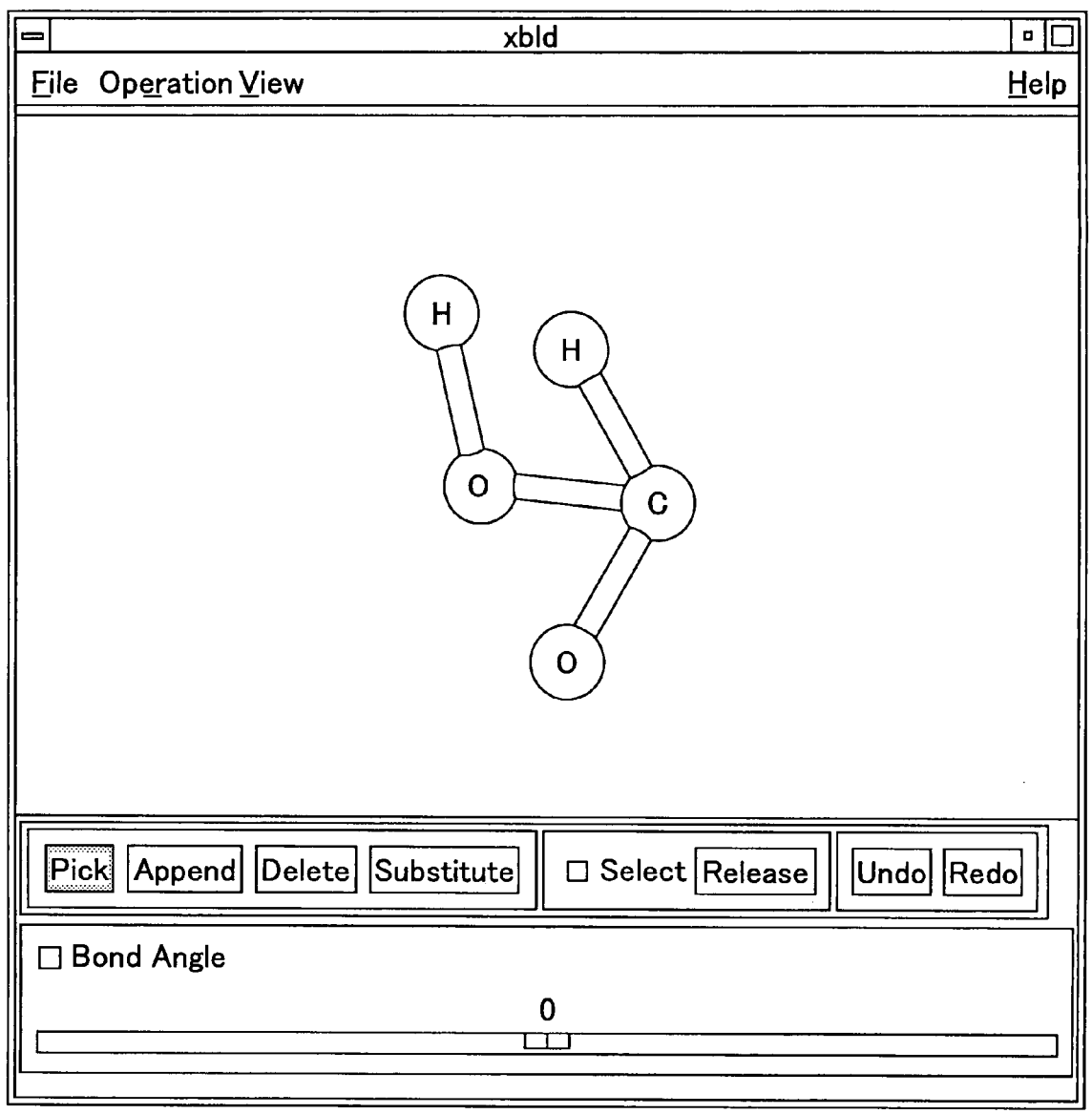
FIG. 25 is a diagram showing a display screen when making the angle modifying operation between two axes.

FIG. 21 is a diagram for explaining the angle modification between two axes by taking the formic acid (HCOOH) as an example. FIGS. 22 and 23 are flow charts for explaining the angle modification between two axes, and FIGS. 24 and 25 are diagrams showing a display screen when making the angle modification between two axes. FIG. 22 shows the process from the operation of selecting the bond axis item (also the atom item if necessary) up to the setting of a ring existence flag, and FIG. 23 shows the process from the setting of the rotation target and the rotation computation up to the actual modification of the structure.

In FIG. 22, a step S131 selects two arbitrary continuous bond axes Bi and Bi'. It is assumed for the sake of convenience that terminal atoms of the bond axes Bi and Bi' are $A_B$, $A_{BB'}$ and $A_{B'}$. A step S132 sets a rotation angle adjusting flag of the two bond axes Bi and Bi', that is, sets the "angle modification between two axes" bit to the event information flag of the molecular data. A step S133 judges whether or not only the bond axes Bi and Bi' are selected as the bond axes and no atom is selected or only the terminal atom $A_B$ (or $A_{B'}$) is selected. If the judgement result in the step S133 is NO, the process advances to a step S158 shown in FIG. 23 which will be described later. On the other hand, if the judgement result in the step S133 is YES, a step S134 judges whether or not the terminal atom $A_B$ (or $A_{B'}$) has a bond axis Bi'' that is not yet set. If the judgement result in the step S134 is NO, the process advances to a step S142 shown in FIG. 23 which will be described later.

If the judgement result in the step S134 is YES, a step S135 sets the attribute of the bond axis Bi" to $R_B$ (or $R_{B'}$), and moves to the terminal atom opposite to the terminal atom $A_B$ (or $A_{B'}$) with respect to the bond axis Bi". A step S136 judges whether or not the present atom has a bond axis that has not yet been set. If the judgement result in the step S136 is YES, a step S137 sets the attribute of the bond axis that is not yet set to $R_B$ (or $R_{B'}$), and moves to the terminal atom on the opposite end. If the judgement result in the step S136 is NO, a step S138 moves to the immediately preceding atom, that is, the atom on the opposite end of the bond axis that is set. After the step S137 or S138, a step S139 judges whether or not the present atom is $A_{B'}$ (or $A_B$) or $A_{BB''}$. If the judgement result in the step S139 is NO, a step S140 judges whether or not the present atom is $A_B$ (or $A_{B'}$). On the other hand, if the judgement result in the step S139 is YES, a step S141 sets "true" to the ring existence flag (sets the ring bit of the identification flag). If the judgement result in the step S140 is YES, the process returns to the step S134. If the judgement result in the step S140 is NO or, after the step S141, the process returns to the step S136.

In FIG. 23, the step S142 judges whether or not the ring existence flag is "false" (the ring bit of the identification flag is not set). If the judgement result in the step S142 is NO, the process advances to the step S158 which will be described later. If the judgement result in the step S142 is YES, a step S143 judges whether or not the atom $A_B$ (or $A_{B'}$) has been selected. If the judgement result in the step S143 is YES, a step S144 judges that the bond axis B (or B') is a fixed axis. If the judgement result in the step S143 is NO, a step S145 judges whether or not the atom number of the attribute $R_B$ is lager than the atom number of the attribute $R_{B''}$. If he judgement result in the step S145 is YES, a step S146 sets the bond axis Bi to the fixed axis. If the judgement result in the step S145 is NO, a step S147 sets the bond axis Bi' to the fixed axis. After the step S144 or, the step S146 or, the step S147, the process advances to a step S148.

The step S148 judges whether or not the bond axis Bi (or Bi') is the fixed axis. If the judgement result in the step S148 is YES, a step S149 sets the bond axis of the attribute $R_{B'}$ and the bond axis Bi' to vectors that are the target of the rotation operation, and a step S150 sets a vector that is perpendicular to both the bond axes Bi and Bi' to the rotary axis. On the other hand, if the judgement result in the step S148 is NO, a step S151 sets the bond axis of the attribute $R_B$ and the bond axis Bi to the vectors that are the target of the rotation operation, and the process advances to the step S150.

A step S152 sets an angle formed by the bond axes Bi and Bi' to the initial value of the bond angle. A step S153 adjusts the bond angle. A step S154 acquires rotation angle information corresponding to a difference between the previous rotation angle and the present rotation angle, and carries out a rotation operation with respect to the vector that is the target (that is, the target vector). A step S155 reforms the molecular structure by modifying the atomic coordinates based on the acquired vector information. A step S156 judges whether or not the adjustment of the bond angle has ended, and the process returns to the step S153 if the judgement result in the step S156 is NO. If the judgement result in the step S156 is YES, a step S157 clears (or resets) the selection of the bond axis that is the rotation operation target. In addition, the step S158 clears (or resets) the set information, and the process ends.

Accordingly, first, the bond axes B1 and B2 and the atom A2 shown in FIG. 21 are selected. Since the bond axes B1 and B2 are linked and the atom A2 is a terminal atom of the bond axis B1 and is not a terminal atom of the bond axis B2, the process can reach the second half of the process (algorithm) shown in FIG. 22. When the rotation angle adjusting flag is set (the "angle modification between two axes" bit is set to the event information flag of the molecular data) after this selection, a bond axis set (or group) $R_{A3}$ (B4) linked to the bond axes not including the bond axis B2 is selected using the terminal atom A3, which is the terminal atom of the bond axis B2 but not a terminal atom of the bond axis B1, as the base point according to a recursive process (algorithm) in the second half of the process shown in FIG. 22, and a check is made to determine whether or not the ring existence flag is to be set to "true" (whether or not to set the ring bit of the identification flag belonging to the terminal atom A1, which is the terminal atom of both the bond axes B1 and B2) with respect to the bond axis set $R_{A3}$. If the ring existence flag of the bond axis set $R_{A3}$ is "true", the rotation operation target no longer exists, and thus, the set information is cleared and the rotation operation is ended. Because the formic acid (HCOOH) shown in FIG. 24 does not have a ring structure, the rotation operation is possible in this state.

If the rotation operation becomes possible by the processes described above, the selection bit is set to the bond axis B4 included in the bond axis set $R_{A3}$ and the selected bond axis B2 that does not include the atom A2 as its terminal atom, so as to set the bond axes B4 and B2 as the rotation target, by the first half of the process (algorithm) shown in FIG. 23. The rotary axis is set to an outer product vector of a vector V1 having the direction A1→A2 in a direction of the bond axis B1 and a vector V2 having the direction A1→A3 in a direction of the bond axis B2. This embodiment uses an algorithm that determines the rotation array from the rotary axis and the rotation angle, by displaying a slide bar in the command window that is displayed in the main window, and determining the rotation angle by a drag-and-drop of the slide bar by the mouse 104. The initial angle of the slide bar in FIG. 24 is displayed by computing the initial angle in the initial molecular structure. When the rotation array is determined, the bond axes B2 and B4 are subjected to a rotation computation (or operation) by the second half of the process (algorithm) shown in FIG. 23 and become bond axes B'2 and B'4, and the Cartesian coordinates of the atoms A3 and A5 are modified to A'3 and A'5 by adding the vector from the atom A1, so as to modify the molecular structure in the main window. When the mouse 104 is released, it is regarded that the rotation has ended, and the rotation operation is ended by clearing the selection information and the set information. By these operations, the three-dimensional molecular structure displayed in the main window on the screen 102a of the display 102 becomes as shown in FIG. 25. FIG. 25 shows the result for a case where a rotation from the initial angle of 120 degrees to −66 degrees is made by the drag-and-drop of the mouse 104.

In FIG. 21, it is assumed for the sake of convenience that B1 and B2 are the selected bond axes, the ring flag is "false", A2 is the atom at the fixed end, B2 and B4 are the bond axes that are the rotation target, and A1→A2×A1→A3 is the rotary axis. If the rotation computation is denoted by R, B'2=RB2 and B'4=RB4 stand, and the coordinate modifications of A3 and A5 are respectively represented by A'3=A1+B'2 and A'5=A'3+B'4.

(Modification of Dihedral Angle)

Figure 26:
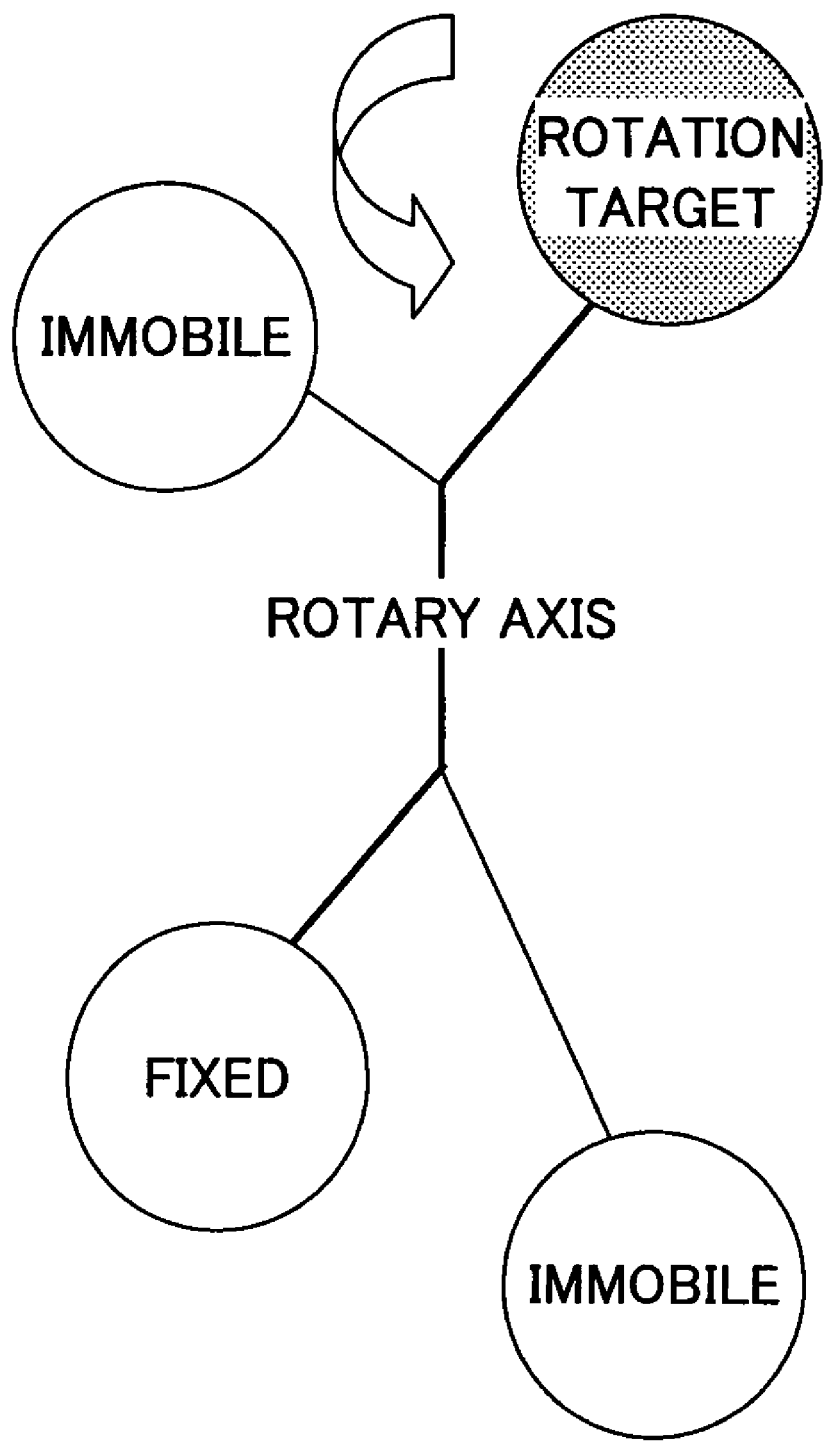
FIG. 26 is a diagram for explaining a modification of a dihedral angle.

FIG. 26 is a diagram for explaining a modification of a dihedral angle. FIG. 26 shows a state where the atom that is the rotation target is bonded to a fixed atom and immobile atoms via bond axis that is a rotary axis.

With respect to the data structures shown in FIG. 1 prepared by the user by the process shown in FIG. 7, three items of the bond axis data structure B are selected. If it is assumed for the sake of convenience that the selected items are identification numbers b1, b2 and b3, a selection bit of the event flag belonging to the bond axis data having the identification numbers b1, b2 and b3 is set. In this state, when the event information of the molecule data structure M is set to "modification of dihedral angle", a "modification of dihedral angle" bit is set in the event flag of the molecule data structure M, by regarding that the bond axis data structure B has three continuous (linked) the bond axis data only when the atomic data of one of the terminal atoms belonging to the bond axis data having the identification number b1 includes the bond axis having the identification number b1 (b3) and the atomic data of one of the terminal atoms belonging to the bond axis data having the identification number b2 (b3) includes the bond axis having the identification number b3 (b2). The selection bit of the identification flag of all bond axis set data linked by bond axes other than the bond axis data having the identification numbers ab1 to b1 (or other than the bond axis data having the identification numbers ab3 (ab2) to b3 (b2)) is set, with respect to both terminal atoms (having identification numbers ab1 and ab3 (ab2)) of the bond axis data having the identification numbers b1 and b3 (b2). If the terminal atoms of the bond axis include the atom having the identification number ab2 (or ab3), it is determined that the bond axis data having the identification numbers b1 and b2 (b3) (or, having the identification number b3 and b2 (b1)) belong to the inside of a ring structure. In this case, a ring bit of the identification flag belonging to the terminal atom data is set. With respect to the bond axis set belonging to the terminal atom data in which the ring bit is set, the selection bit of the identification flag is cleared (or reset) so as to exclude the bond axis set from the target of the rotation operation. If the ring bit is not set, the number of selection bits of the bond axes linked from the atom having the identification number ab1 and the number of selection bits of the bond axes linked from the atom having the identification number ab3 (ab2) are compared, and the smaller number of selection bits is maintained while the larger number of selection bits is cleared (or reset). Thereafter, the bond axis having the selection bit is represented as the rotation target.

If not only the three continuous bond axes but one of the two terminal atoms is also selected, the operation described above is carried out only with respect to the bond axis set linked to the selected atom or the atom that is not selected.

The dihedral angle is computed by making a drag-and-drop by the pointing device on the displayed molecular structure or, is determined by making a drag-and-drop in a command area other than a molecule display area in the main window or by setting the angle from the keyboard, and the process moves to the rotation operation. When the dihedral angle is specified by the drag-and-drop, the rotation operation is continuously carried during the dragging.

The rotation operation sets the "modification of dihedral angle" bit to the event flag of the bond axis data having the specified identification numbers b1, b2 and b3, and sets to the rotary axis a vector v3 that is perpendicular to both a vector v1 that is perpendicular to both the bond axes having the identification numbers b1 and b2 (b3) and a vector v2 that is perpendicular to both the bond axes having the identification numbers b2 and b3. The direction of the rotary axis is taken from the fixed end towards the rotation target. The rotation operation computes the rotation array or the quaternion from the rotary axis and the rotation angle, and makes the rotation array or the quaternion act on the bond axis that is the rotation target. Thereafter, the vector information of the bond axis is traced from one appropriate atom so as to reform the Cartesian coordinates of the atom data structure A, and the modified molecular structure is displayed in the main window.

Figure 27:
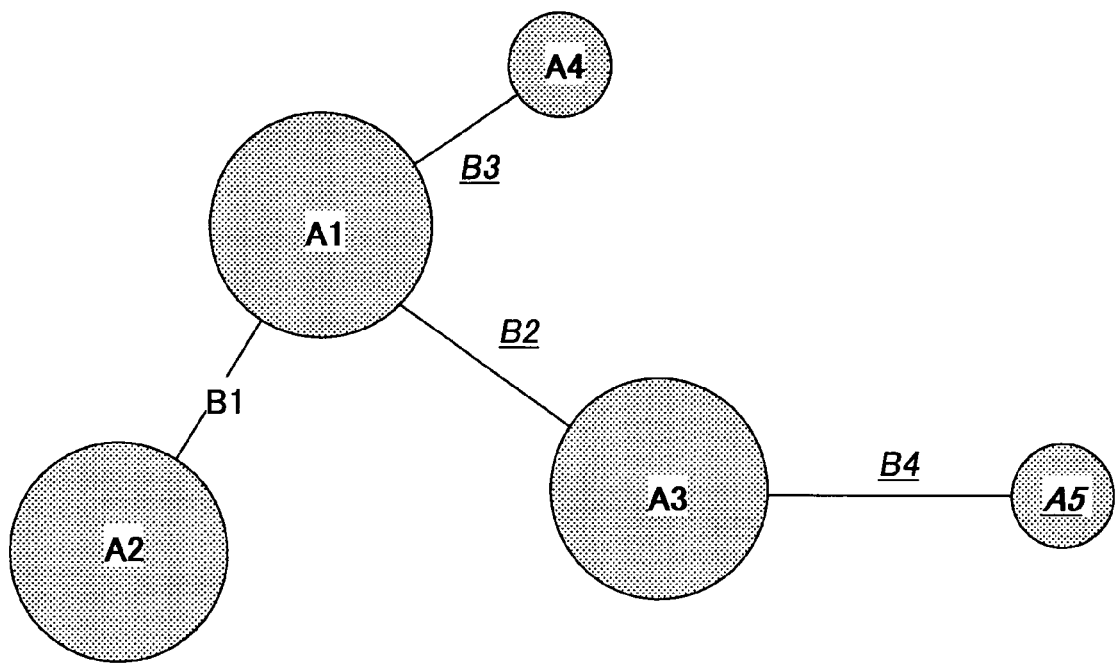
FIG. 27 is a diagram for explaining the modification of the dihedral angle by taking formic acid (HCOOH) as an example.
Figure 28:
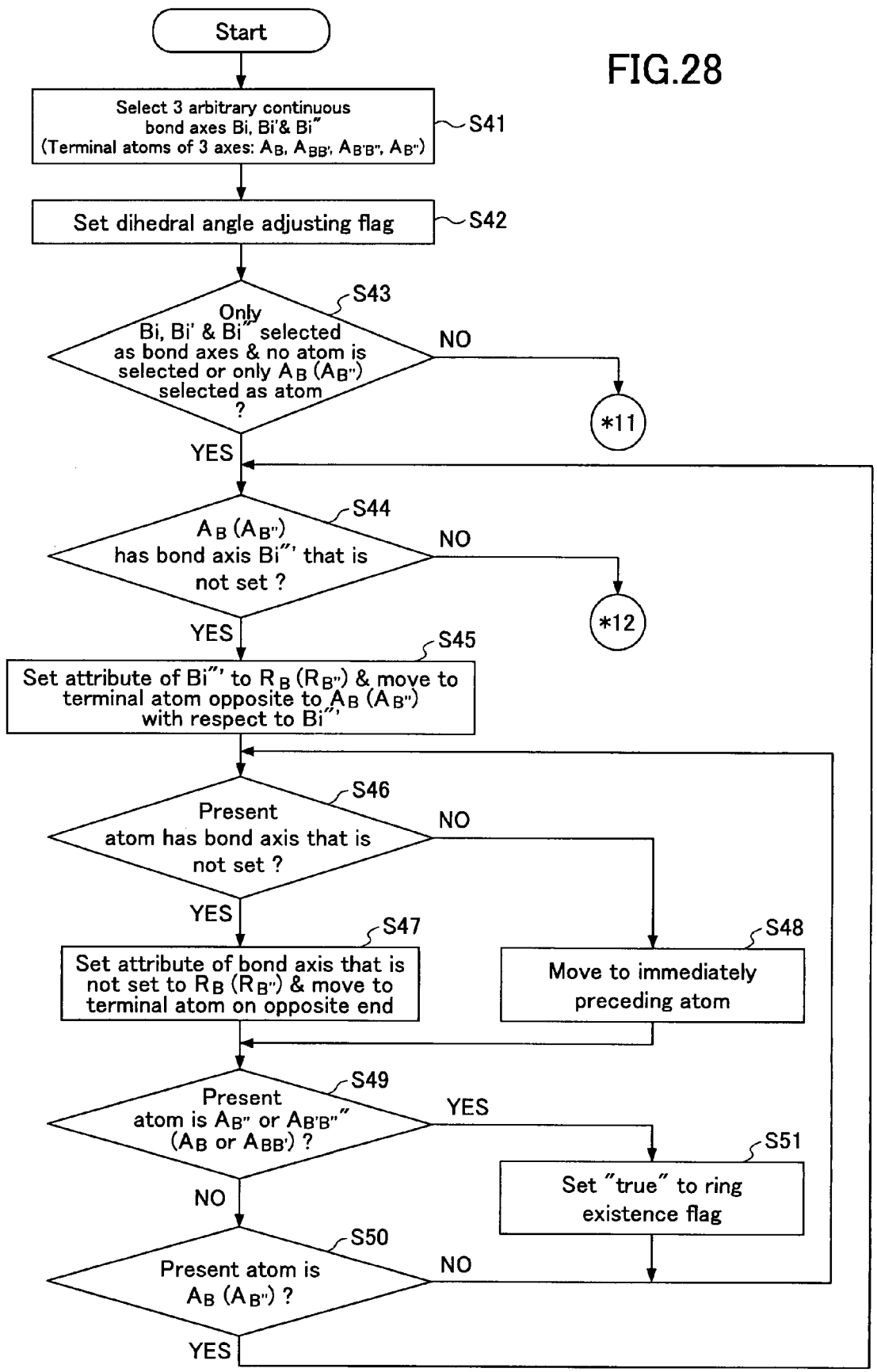
FIG. 28 is a flow chart for explaining the modification of the dihedral angle.
Figure 29:
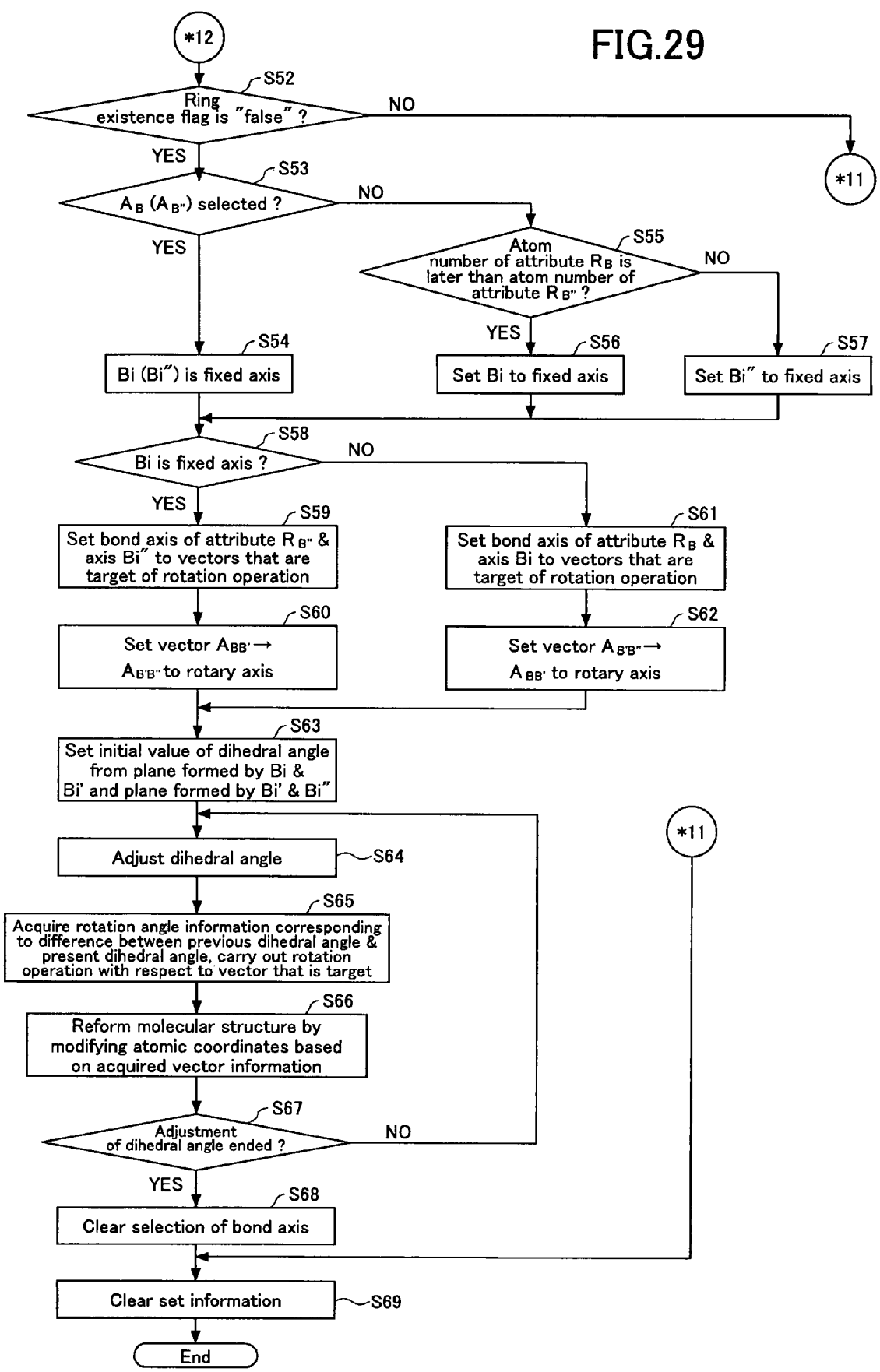
FIG. 29 is a flow chart for explaining the modification of the dihedral angle.
Figure 30:
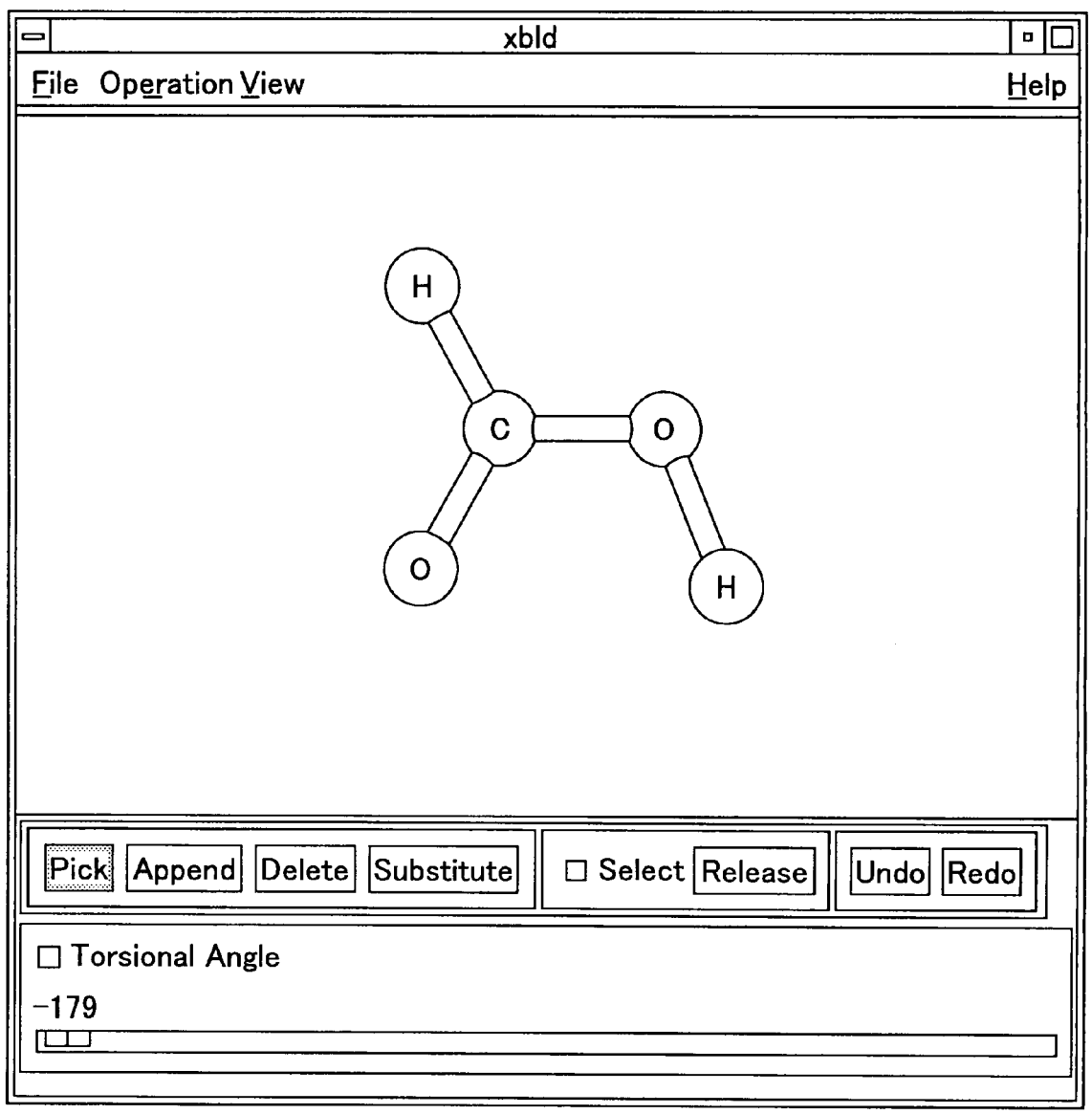
FIG. 30 is a diagram showing a display screen when making a modifying operation of the dihedral angle.
Figure 31:
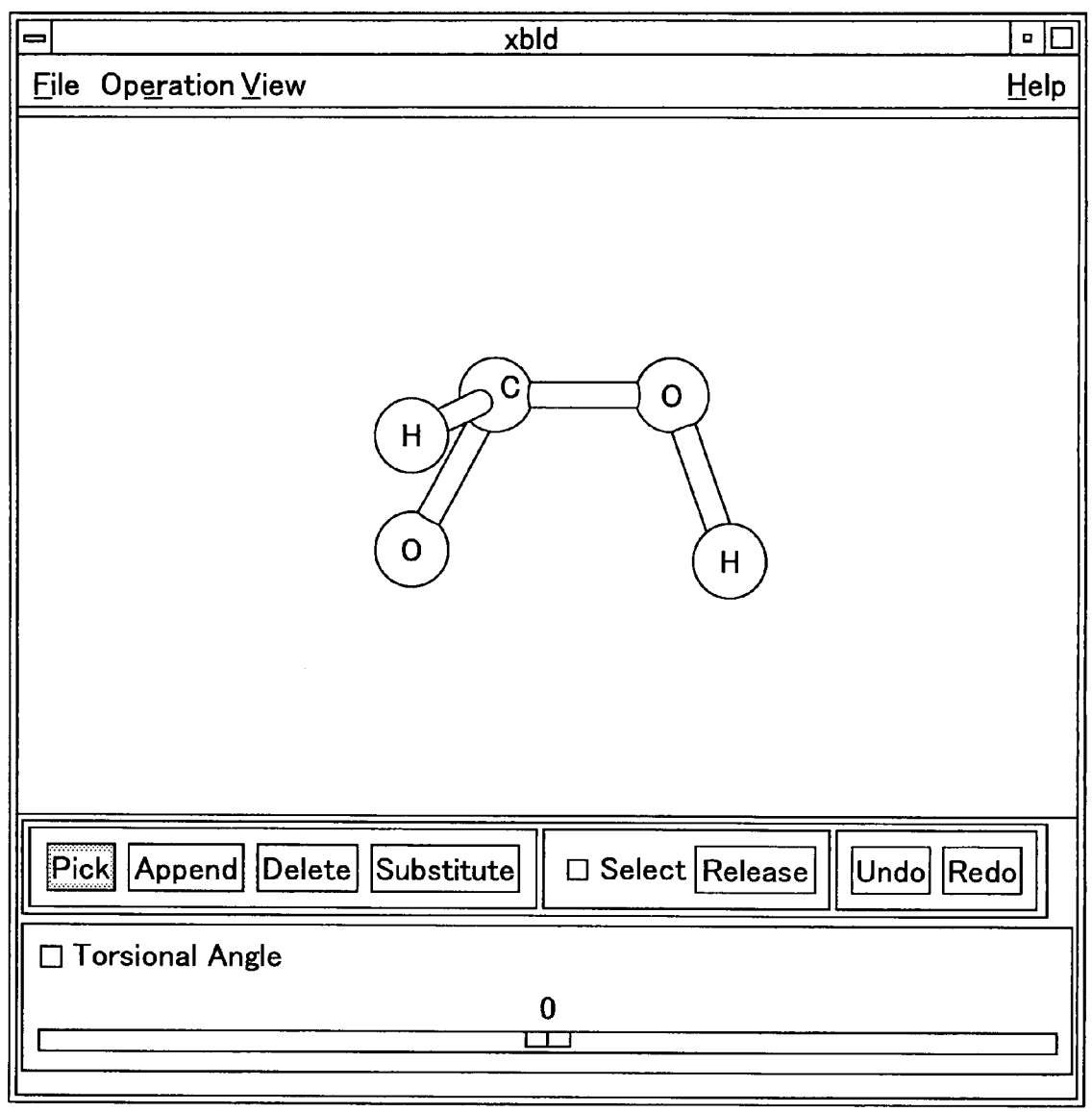
FIG. 31 is a diagram showing a display screen when making the modifying operation of the dihedral angle.

FIG. 27 is a diagram for explaining the modification of the dihedral angle by taking the formic acid (HCOOH) as an example. FIGS. 28 and 29 are flow charts for explaining the modification of the dihedral angle, and FIGS. 30 and 31 are diagrams showing a display screen when making the modification of the dihedral angle. FIG. 30 shows the process from the operation of selecting the bond axis item (also the atom item if necessary) up to the setting of a ring existence flag, and FIG. 31 shows the process from the setting of the rotation target and the rotation computation up to the actual modification of the structure.

In FIG. 28, a step S41 selects three arbitrary continuous bond axes Bi, Bi' and Bi". It is assumed for the sake of convenience that terminal atoms of the bond axes Bi, Bi' and Bi" are $A_{Bi}$, $A_{BiBi'}$, $A_{Bi'Bi''}$, and $A_{Bi''}$. A step S42 sets a dihedral angle adjusting flag of the three bond axes Bi, Bi' and Bi", that is, sets the "modification of dihedral angle" bit to the event information flag of the molecular data. A step S43 judges whether or not only the bond axes Bi, Bi' and Bi" are selected as the bond axes and no atom is selected or only the terminal atom $A_{Bi}$ (or $A_{Bi''}$) is selected. If the judgement result in the step S43 is NO, the process advances to a step S69 shown in FIG. 29 which will be described later. On the other hand, if the judgement result in the step S43 is YES, a step S44 judges whether or not the terminal atom $A_{Bi}$ (or $A_{Bi''}$) has a bond axis Bi''' that is not yet set. If the judgement result in the step S44 is NO, the process advances to a step S52 shown in FIG. 29 which will be described later.

If the judgement result in the step S44 is YES, a step S45 sets the attribute of the bond axis Bi''' to $R_{Bi}$ (or $R_{Bi''}$), and moves to the terminal atom opposite to the terminal atom $A_{Bi}$ (or $A_{Bi}$") with respect to the bond axis Bi'''. A step S46 judges whether or not the present atom has a bond axis that has not yet been set. If the judgement result in the step S46 is YES, a step S47 sets the attribute of the bond axis that is not yet set to $R_{Bi}$ (or $R_{Bi''}$), and moves to the terminal atom on the opposite end. If the judgement result in the step S46 is NO, a step S48 moves to the immediately preceding atom, that is, the atom on the opposite end of the bond axis that is set. After the step S47 or S48, a step S49 judges whether or not the present atom is $A_{Bi''}$ or $A_{Bi'Bi''}$ (or, $A_{Bi}$ or $A_{BiBi'}$). If the judgement result in the step S49 is NO, a step S50 judges whether or not the present atom is $A_{Bi}$ (or $A_{Bi''}$). On the other hand, if the judgement result in the step S49 is YES, a step S51 sets "true" to the ring existence flag (sets the ring bit of the identification flag). If the judgement result in the step S50 is YES, the process returns to the step S44. If the judgement result in the step S50 is NO or, after the step S51, the process returns to the step S46.

In FIG. 29, the step S52 judges whether or not the ring existence flag is "false" (the ring bit of the identification flag is not set). If the judgement result in the step S52 is NO, the process advances to the step S69 which will be described later. If the judgement result in the step S52 is YES, a step S53 judges whether or not the atom $A_{Bi}$ (or $A_{Bi''}$) has been selected. If the judgement result in the step S53 is YES, a step S54 sets the atom $A_{Bi}$ (or $A_{Bi''}$) to the fixed end. If the judgement result in the step S53 is NO, a step S55 judges whether or not the atom number of the attribute $R_{Bi}$ is lager than the atom number of the attribute $R_{Bi''}$. If he judgement result in the step S55 is YES, a step S56 sets the atom $A_{Bi}$ to the fixed end. If the judgement result in the step S55 is NO, a step S57 sets the atom $A_{Bi''}$ to the fixed end. After the step S54 or, the step S56 or, the step S57, the process advances to a step S58.

The step S58 judges whether or not the atom $A_{Bi}$ is the fixed end. If the judgement result in the step S58 is YES, a step S59 sets the bond axis of the attribute $R_{Bi''}$ and the bond axis Bi'' to vectors that are the target of the rotation operation, and a step S60 sets a vector $A_{BiBi''} \rightarrow A_{BiBi''}$ to the rotary axis. On the other hand, if the judgement result in the step S58 is NO, a step S61 sets the bond axis of the attribute $R_{Bi}$ and the bond axis Bi to the vectors that are the target of the rotation operation, and a step S62 sets a vector $A_{Bi'Bi''} \rightarrow A_{BiBi''}$ to the rotary axis. After the step S60 or S62, the process advances to a step S63.

The step S63 sets the initial value of the dihedral angle from the plane (or surface) that is formed by the bond axis Bi and Bi' and a plane (or surface) that is formed by the bond axis Bi' and Bi''. A step S64 adjusts the dihedral angle. A step S65 acquires rotation angle information corresponding to a difference between the previous dihedral angle and the present dihedral angle, and carries out a rotation operation with respect to the vector that is the target (that is, the target vector). A step S66 reforms the molecular structure by modifying the atomic coordinates based on the acquired vector information. A step S67 judges whether or not the adjustment of the dihedral angle has ended, and the process returns to the step S64 if the judgement result in the step S67 is NO. If the judgement result in the step S67 is YES, a step S68 clears (or resets) the selection of the bond axis that is the rotation operation target. In addition, the step S69 clears (or resets) the set information, and the process ends.

Accordingly, first, the bond axes B2, B3 and B4 and the atom A5 shown in FIG. 27 are selected. Since the bond axes B2, B3 and B4 are linked and the atom A5 is a terminal atom of the bond axis B4 and is not a terminal atom of the bond axis B2, the process can reach the second half of the process (algorithm) shown in FIG. 28. When the rotation angle adjusting flag is set (the "modification of dihedral angle" bit is set to the event information flag of the molecular data) after this selection, a bond axis set (or group) $R_{A1}$ (B3) linked to the bond axes including the bond axis B3 but not including the bond axis B2 is selected using the terminal atom A1, which is the terminal atom of the bond axis B2 and a terminal atom of the bond axis B3, as the base point according to a recursive process (algorithm) in the second half of the process shown in FIG. 28, and a check is made to determine whether or not the ring existence flag is to be set to "true" (whether or not to set the ring bit of the identification flag belonging to the terminal atom A3, which is the terminal atom of both the bond axes B2 and B4) with respect to the bond axis set $R_{A1}$. If the ring existence flag of the bond axis set $R_{A1}$ is "true", the rotation operation target no longer exists, and thus, the set information is cleared and the rotation operation is ended. By these operations, the three-dimensional molecular structure displayed in the main window on the screen 102a of the display 102 becomes as shown in FIG. 30. Because the formic acid (HCOOH) shown in FIG. 30 does not have a ring structure, the rotation operation is possible in this state.

If the rotation operation becomes possible by the processes described above, the selection bit is set to the bond axis B3 included in the bond axis set $R_{A1}$, so as to set the bond axis B3 as the rotation target, by the first half of the process (algorithm) shown in FIG. 29. The rotary axis of the bond axis B3 is set to a vector having the direction A3→A1 in a direction of the bond axis B2. This embodiment uses an algorithm that determines the rotation array from the rotary axis and the rotation angle, by displaying a slide bar in the command window that is displayed in the main window, and determining the rotation angle by a drag-and-drop of the slide bar by the mouse 104. The initial angle of the slide bar in FIG. 30 is displayed by computing the initial angle in the initial molecular structure. When the rotation array is determined, the bond axis B3 is subjected to a rotation computation (or operation) by the second half of the process (algorithm) shown in FIG. 29 and becomes a bond axes B'3, and the Cartesian coordinates of the atoms A4 are modified to A'4 by adding the vector from the atom A1, so as to modify the molecular structure in the main window. When the mouse 104 is released, it is regarded that the rotation has ended, and the rotation operation is ended by clearing the selection information and the set information. By these operations, the three-dimensional molecular structure displayed in the main window on the screen 102a of the display 102 becomes as shown in FIG. 31. FIG. 31 shows the result for a case where a rotation from the initial dihedral angle of −179 degrees to 74 degrees is made by the drag-and-drop of the mouse 104.

In FIG. 27, it is assumed for the sake of convenience that B2, B3, B4 and B5 are the selected bond axes, the ring flag is "false", A5 is the atom at the fixed end, B3 is the bond axis that is the rotation target, and A3→A1 is the rotary axis. If the rotation computation is denoted by R, B'3=RB3 stands, and the coordinate modification of A4 is represented by A'4=A1+B'3.

(Expansion and Contraction of Bond Axis)

Figure 32:
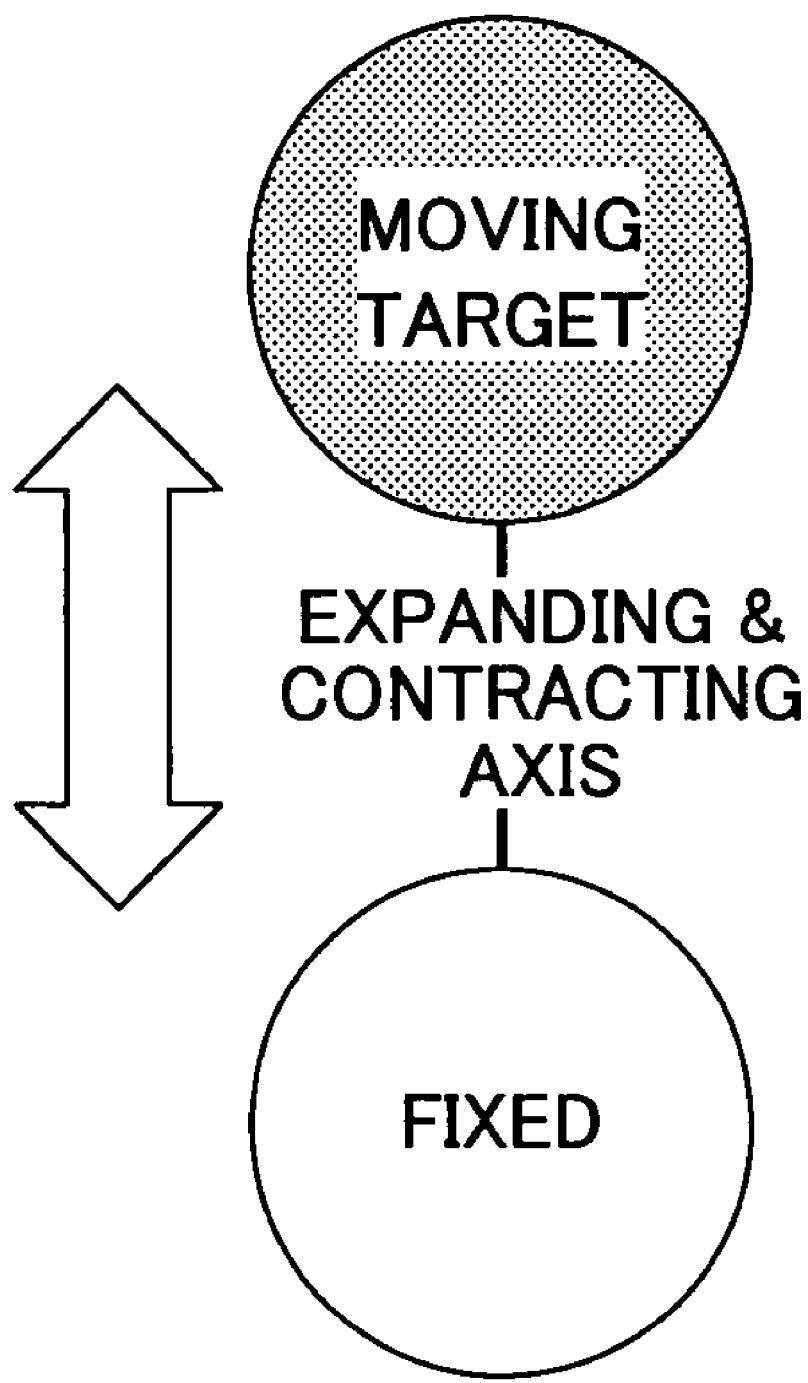
FIG. 32 is a diagram for explaining expansion and contraction of a bond axis.

FIG. 32 is a diagram for explaining expansion and contraction of the bond axis. FIG. 32 shows a state where the atom that is the moving target is bonded to a fixed atom via a bond axis that is an expanding and contracting axis.

With respect to the data structures shown in FIG. 1 prepared by the user by the process shown in FIG. 7, one item of the bond axis data structure B is selected. If it is assumed for the sake of convenience that the selected item is an identification number b1, a selection bit of the event flag belonging to the bond axis data having the identification number b1 is set. In this state, when the event information of the molecule data structure M is set to "expansion and contraction", a "expansion and contraction" bit is set in the event flag of the molecule data structure M, and the selection bit of the identification flag of all bond axis set data linked by bond axes other than the bond axis data having the identification number b1 is set, with respect to both terminal atoms (having identification numbers a1 and a2) of the bond axis data having the identification number b1. If the terminal atoms of the bond axis include the atom having the identification number a1 or a2, it is determined that the bond axis data having the identification number b1 belongs to the inside of a ring structure. In this case, a ring bit of the identification flag belonging to the terminal atom data is set. With respect to the bond axis set belonging to the terminal atom data in which the ring bit is set, the selection bit of the identification flag is cleared (or reset) so as to exclude the bond axis set from the target of the expansion and contraction operation. If the ring bit is not set, the number of selection bits of the bond axes linked from the atom having the identification number a1 and the number of selection bits of the bond axes linked from the atom having the identification number a2 are compared, and the smaller number of selection bits is maintained while the larger number of selection bits is cleared (or reset). Thereafter, the bond axis having the selection bit is represented as the moving target.

If not only the bond axis but one of the terminal atoms is also selected, the operation described above is carried out only with respect to the bond axis set linked to the selected atom or the atom that is not selected.

The contraction scale is computed by making a drag-and-drop by the pointing device on the displayed molecular structure or, is determined by making a drag-and-drop in a command area other than a molecule display area in the main window or by setting the contraction scale from the keyboard, and the process moves to the expansion and contraction operation. When the contraction scale of the bond axis is specified by the drag-and-drop, the expansion and contraction rotation operation is continuously carried during the dragging.

The expansion and contraction operation sets the "expansion and contraction" bit to the event flag of the bond axis data having the specified identification number b1, and modifies the vector information of the bond axis having the identification number b1 depending on the contraction scale. Thereafter, the vector information of the bond axis that is the target of the expansion and contraction operation is traced from the terminal atom of the bond axis having the identification number b1 so as to reform the Cartesian coordinates of the atom data structure A, and the modified molecular structure is displayed in the main window.

Figure 33:
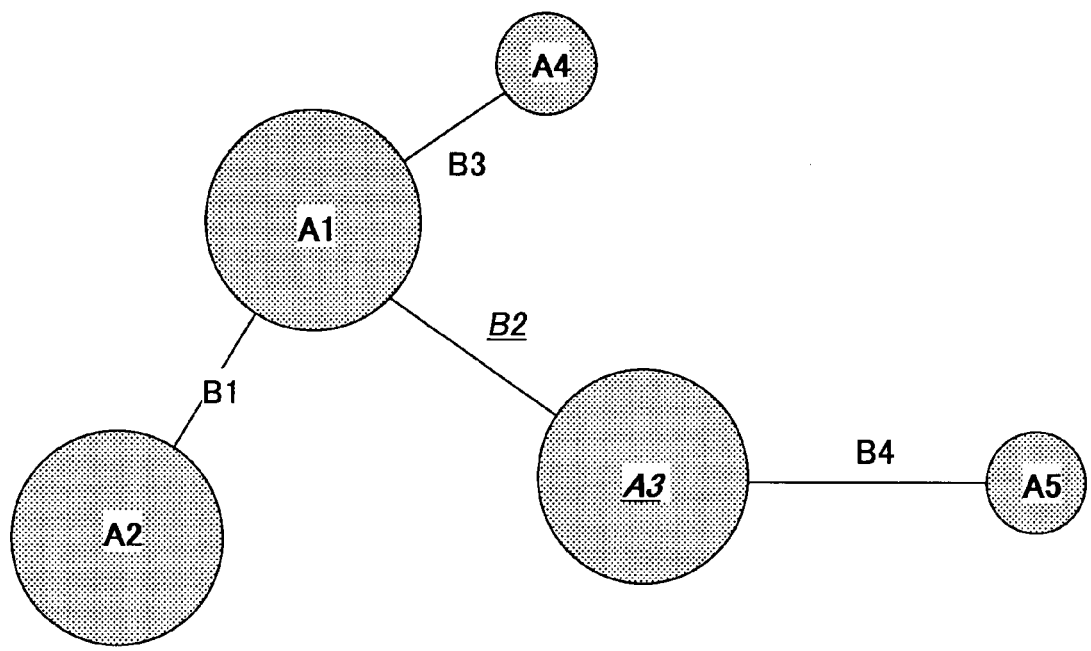
FIG. 33 is a diagram for explaining the expansion and contraction of the bond axis by taking formic acid (HCOOH) as an example.
Figure 34:
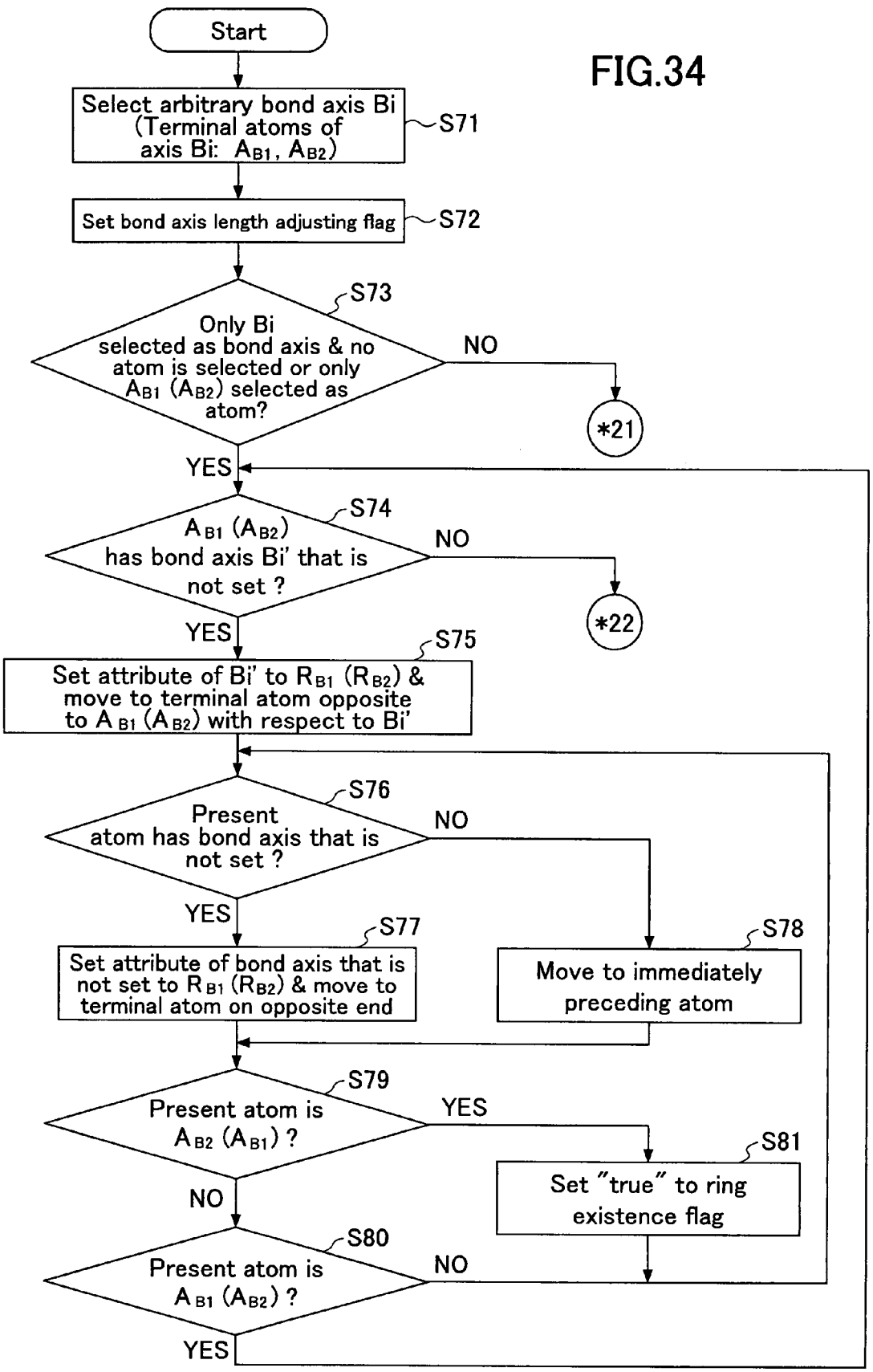
FIG. 34 is a flow chart for explaining the expansion and contraction of the bond axis.
Figure 35:
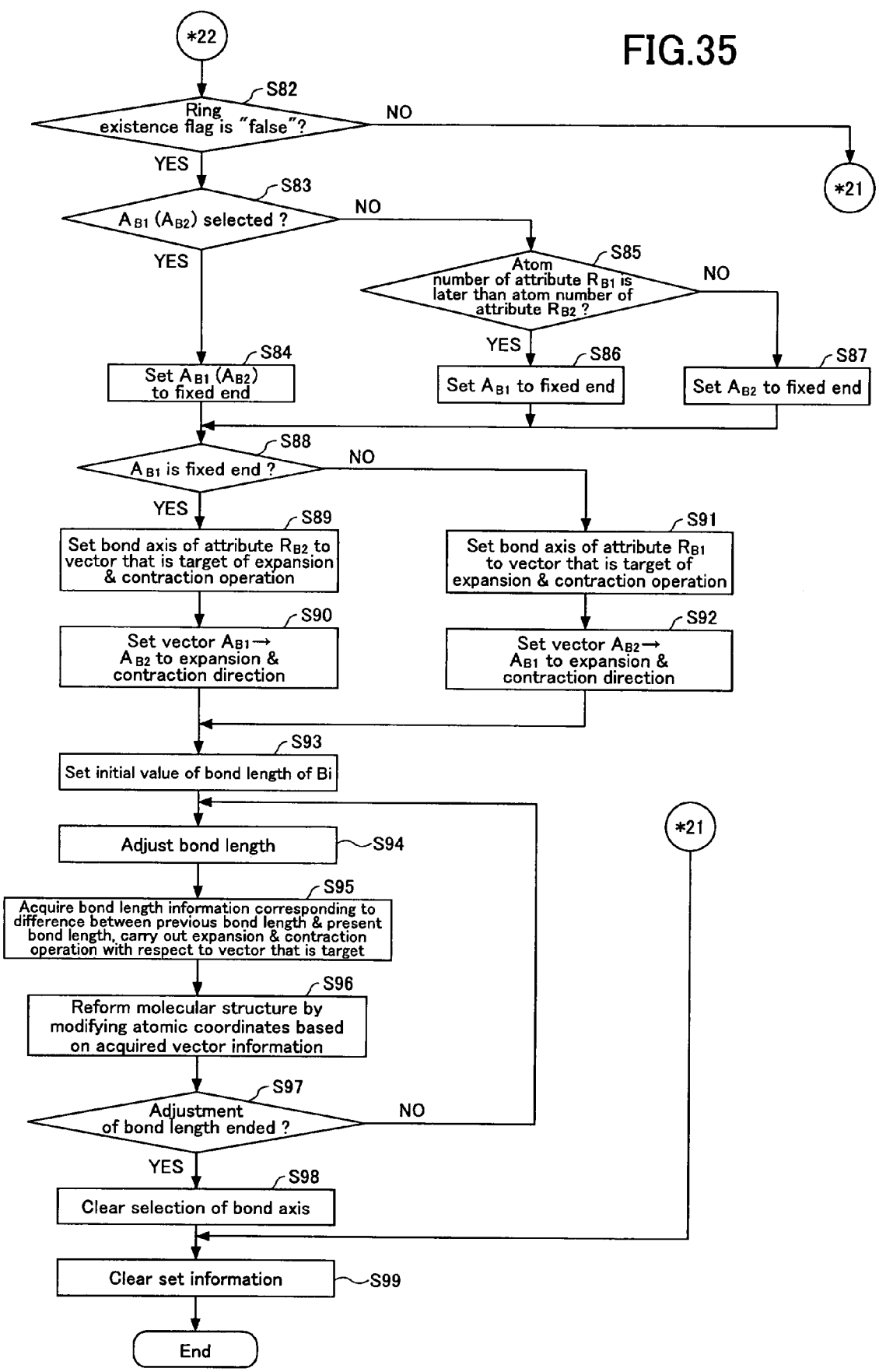
FIG. 35 is a flow chart for explaining the expansion and contraction of the bond axis.
Figure 36:
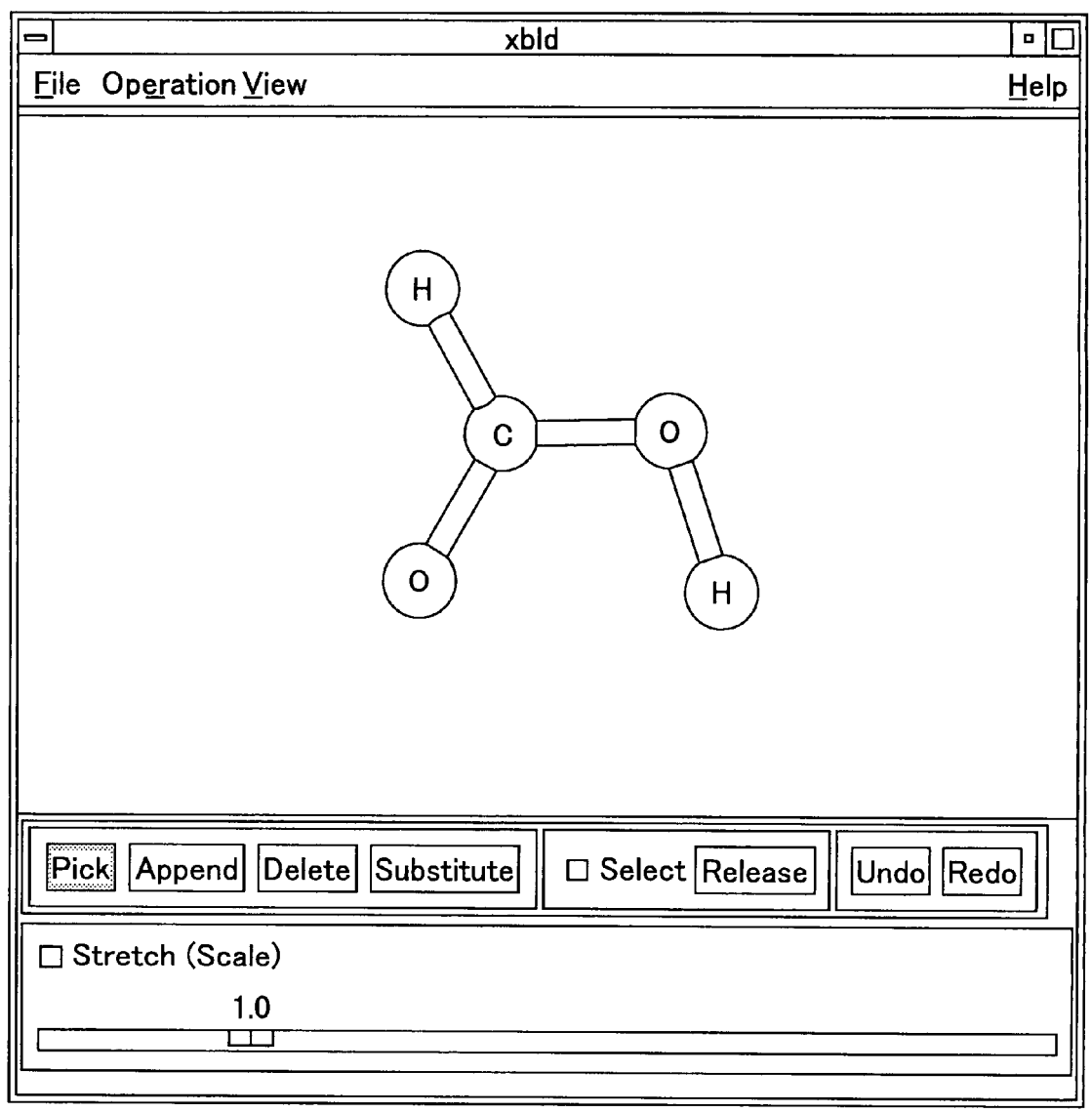
FIG. 36 is a diagram showing a display screen when making the expansion and contraction operation of the bond axis.
Figure 37:
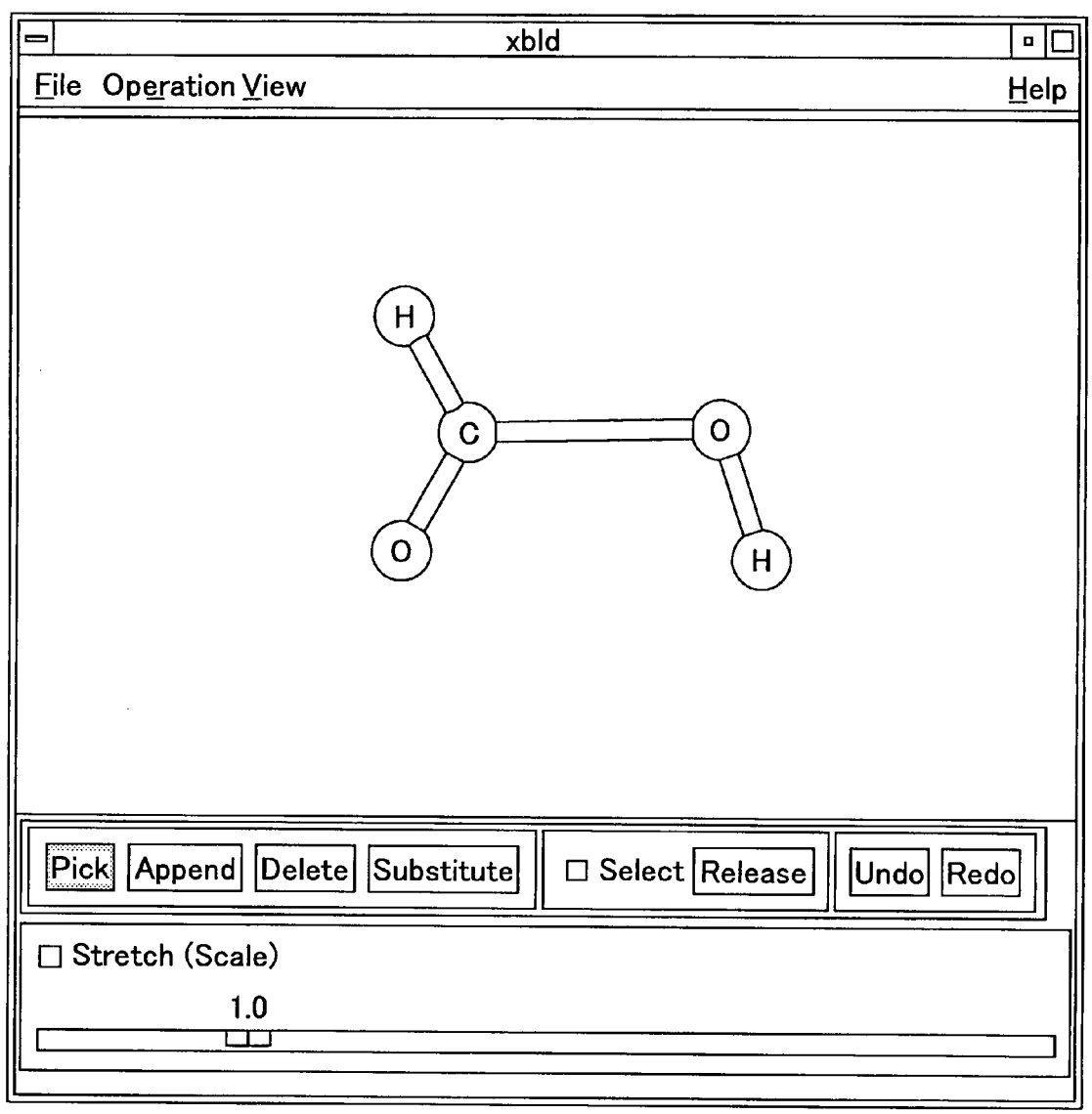
FIG. 37 is a diagram showing a display screen when making the expansion and contraction operation of the bond axis.

FIG. 33 is a diagram for explaining the expansion and contraction of the bond axis by taking the formic acid (HCOOH) as an example. FIGS. 34 and 35 are flow charts for explaining the expansion and contraction of the bond axis, and FIGS. 36 and 37 are diagrams showing a display screen when making the expansion and contraction operation. FIG. 36 shows the process from the operation of selecting the bond axis item (also the atom item if necessary) up to the setting of a ring existence flag, and FIG. 37 shows the process from the setting of the moving target and the expansion and contraction computation up to the actual modification of the structure.

In FIG. 34, a step S71 selects an arbitrary bond axis Bi. It is assumed for the sake of convenience that terminal atoms of the bond axis Bi are $A_{B1}$ and $A_{B2}$. A step S72 sets a bond axis length adjusting flag of the bond axis Bi, that is, sets the "expansion and contraction" bit to the event information flag of the molecular data. A step S73 judges whether or not only the bond axis Bi is selected as the bond axis and no atom is selected or only the terminal atom $A_{B1}$ (or $A_{B2}$) is selected. If the judgement result in the step S73 is NO, the process advances to a step S99 shown in FIG. 35 which will be described later. On the other hand, if the judgement result in the step S73 is YES, a step S74 judges whether or not the terminal atom $A_{B1}$ (or $A_{B2}$) has a bond axis Bi' that is not yet set. If the judgement result in the step S74 is NO, the process advances to a step S82 shown in FIG. 35 which will be described later.

If the judgement result in the step S74 is YES, a step S75 sets the attribute of the bond axis Bi' to $R_{B1}$ (or $R_{B2}$), and moves to the terminal atom opposite to the terminal atom $A_{B1}$ (or $A_{B2}$) with respect to the bond axis Bi'. A step S76 judges whether or not the present atom has a bond axis that has not yet been set. If the judgement result in the step S76 is YES, a step S77 sets the attribute of the bond axis that is not yet set to $R_{B1}$ (or $R_{B2}$), and moves to the terminal atom on the opposite end. If the judgement result in the step S76 is NO, a step S78 moves to the immediately preceding atom, that is, the atom on the opposite end of the bond axis that is set. After the step S77 or S78, a step S79 judges whether or not the present atom is $A_{B2}$ (or $A_{B1}$). If the judgement result in the step S79 is NO, a step S80 judges whether or not the present atom is $A_{B1}$ (or $A_{B2}$). On the other hand, if the judgement result in the step S79 is YES, a step S81 sets "true" to the ring existence flag (sets the ring bit of the identification flag). If the judgement result in the step S80 is YES, the process returns to the step S74. If the judgement result in the step S80 is NO or, after the step S81, the process returns to the step S76.

In FIG. 35, the step S82 judges whether or not the ring existence flag is "false" (the ring bit of the identification flag is not set). If the judgement result in the step S82 is NO, the process advances to the step S99 which will be described later. If the judgement result in the step S82 is YES, a step S83 judges whether or not the atom $A_{B1}$ (or $A_{B2}$) has been selected. If the judgement result in the step S83 is YES, a step S84 sets the atom $A_{B1}$ (or $A_{B2}$) to the fixed end. If the judgement result in the step S83 is NO, a step S85 judges whether or not the atom number of the attribute $R_{B1}$ is lager than the atom number of the attribute $R_{B2}$. If he judgement result in the step S85 is YES, a step S86 sets the atom $A_{B1}$ to the fixed end. If the judgement result in the step S85 is NO, a step S87 sets the atom $A_{B2}$ to the fixed end. After the step S84 or, the step S86 or, the step S87, the process advances to a step S88.

The step S88 judges whether or not the atom $A_{B1}$ is the fixed end. If the judgement result in the step S88 is YES, a step S89 sets the bond axis of the attribute $R_{B2}$ to a vector that is the target of the expansion and contraction operation, and a step S90 sets a vector $A_{B1} \rightarrow A_{B2}$ in an expanding and contracting direction. On the other hand, if the judgement result in the step S88 is NO, a step S91 sets the bond axis of the attribute $R_{B1}$ to the vector that is the target of the expansion and contraction operation, and a step S92 sets a vector $A_{B2} \rightarrow A_{B1}$ in the expanding and contracting direction. After the step S90 or S92, the process advances to the step S93.

The step S93 sets the bond length of the bond axis Bi to the initial value. A step S94 adjusts the bond length. A step S95 acquires bond length information corresponding to a difference between the previous bond length and the present bond length, and carries out an expansion and contraction operation with respect to the vector that is the target (that is, the target vector). A step S96 reforms the molecular structure by modifying the atomic coordinates based on the acquired vector information. A step S97 judges whether or not the adjustment of the bond length has ended, and the process returns to the step S94 if the judgement result in the step S97 is NO. If the judgement result in the step S97 is YES, a step S98 clears (or resets) the selection of the bond axis that is the expansion and contraction operation target. In addition, the step S99 clears (or resets) the set information, and the process ends.

Accordingly, first, the bond axis B2 and the atom A3 shown in FIG. 33 are selected. Since the atom A3 is a terminal atom of the bond axis B2, the process can reach the second half of the process (algorithm) shown in FIG. 34. When the bond length adjusting flag is set (the "expansion and contraction" bit is set to the event information flag of the molecular data) after this selection, a bond axis set (or group) $R_{A1}$ (B1, B3) linked to the bond axes not including the bond axis B2 is selected using the terminal atom A1 as the base point according to a recursive process (algorithm) in the second half of the process shown in FIG. 34, and a check is made to determine whether or not the ring existence flag is to be set to "true" (whether or not to set the ring bit of the identification flag belonging to the terminal atom A3) with respect to the bond axis set $R_{A1}$. If the ring existence flag of the bond axis set $R_{A1}$ is "true", the moving operation target of the expansion and contraction no longer exists, and thus, the set information is cleared and the moving operation is ended. By these operations, the three-dimensional molecular structure displayed in the main window on the screen 102a of the display 102 becomes as shown in FIG. 36. Because the formic acid (HCOOH) shown in FIG. 36 does not have a ring structure, the expansion and contraction operation is possible in this state.

If the expansion and contraction operation becomes possible by the processes described above, the bond axis B2 is set to the expanding and contracting axis, with respect to the bond axes B1 and B3 that are the moving targets and are included in the bond axis set $R_{A1}$, by the first half of the process (algorithm) shown in FIG. 35. This embodiment uses an algorithm that determines the contraction scale by displaying a slide bar in the command window that is displayed in the main window, and determining the contraction scale by a drag-and-drop of the slide bar by the mouse 104. When the contraction scale is determined, the bond axis B2 is subjected to an expansion and contraction computation (or operation) by the second half of the process (algorithm) shown in FIG. 35 and become a bond axis B'2, and the Cartesian coordinates of the atoms A1, A2 and A4 are modified to A'1, A'2 and A'4 by adding the vector from the atom A3, so as to modify the molecular structure in the main window. When the mouse 104 is released, it is regarded that the expansion and contraction has ended, and the expansion and contraction operation is ended by clearing the selection information and the set information. By these operations, the three-dimensional molecular structure displayed in the main window on the screen 102a of the display 102 becomes as shown in FIG. 37. FIG. 37 shows the result for a case where the bond length is expanded to 1.8 times by the drag-and-drop of the mouse 104.

In FIG. 33, it is assumed for the sake of convenience that B2 is the selected bond axis, A3 is the selected atom, the ring flag is "false", A3 is the atom at the fixed end, and B2 is the bond axis that is the expansion and contraction target. If the expansion and contraction computation is denoted by S, B'2=SB2 stands, and the coordinate modifications of A1, A2 and A4 are respectively represented by A'1=A3+B'2, A'2=A'1+B1 and A'4=A'1+B3.

The free rotation around the atom, the rotation around the bond axis, the angle modification between the two axes, the modification of the dihedral angle, and the expansion and contraction of the bond axis described above may be approximately combined. In addition, compared to the conventional technique, it is easier to make the operation to arbitrarily modify the molecular structure and to make the entire operation to form the molecular structure, because the information of two terminal atoms, the vector information and the flag information are included in all of the bond axes, and all bond axis information, coordinates and flag information are included in all of the atoms.

This application claims the benefit of a Japanese Patent Application No. 2006-310564 filed Nov. 16, 2006, in the Japanese Patent Office, the disclosure of which is hereby incorporated by reference.

Further, the present invention is not limited to these embodiments, but various variations and modifications may be made without departing from the scope of the present invention.

What is claimed is:

1. A molecule design support apparatus comprising:
a storage part configured to store, with respect to data having a given three-dimensional molecular structure, an atom data structure A related to an atom, a bond axis data structure B related to a bond axis, and a molecule data structure M related to a molecule;
wherein the atom data structure A includes an identification number "a" made up of an atomic sequence number in internal coordinates, an atom number made up of a chemical symbol, a bond axis number made up of a numerical value that varies when an arbitrary new molecular structure is added to an original molecule, an identification number of the bond axis, made up of a set data of an identification number "b" of each bond axis included in the bond axis number, and an identification flag for use in checking whether or not the molecular structure has a ring structure,
wherein the bond axis data structure B includes an identification number "b" made up of the number that is necessary to make all of the bond axes correspond 1:1 with each other, an identification number of a terminal atom, made up of a set data of the identification number "a" of the atom existing at both terminals of the bond axis, and having a data number is 2, an event flag indicating a present type of event with respect to events of the molecular structure forming a GUI (Graphical User Interface), including a rotation operation, an expansion and contraction operation, a delete operation, an add operation and a replace operation, an identification flag identical to the identification flag of the atom data structure A, and vector information including information indicating a 1:1 correspondence between the bond axis and a three-dimensional vector,
wherein the molecule data structure M includes the atom number, the bond axis number, the atom data structure A, the bond axis data structure B, event information of the event, and the event flag,
an input part;
a display configured to display on a screen thereof the three-dimensional molecular structure by a half vector format or a ball-and-stick format;
a determining part configured to determine, in the molecular structure, an end that is to become a target of a coordinate modification with respect to a molecule in its entirety, in response to a bond axis of the molecule specified from the input part;
a modifying part configured to make a modification of the molecular structure based on the specified bond axis and the end that is the target of the coordinate modification, using information included in the atom data structure A and the bond axis data structure B, in response to the modification specified from the input part, said modification including at least one of a free rotation around an atom, a rotation around a bond axis, an angular modification between two axes, a modification of a dihedral angle, and an expansion and contraction of a bond axis; and
a display part configured to display a modified molecular structure on the screen of the display based on a determination made by the determining part and the modification made by the modifying part.

2. The molecule design support apparatus as claimed in claim 1, wherein:
said determining part determines the end that is to become the target of the coordinate modification with respect to the molecule in its entirety, based on one bond axis of the molecule or, said one bond axis and one of two terminal atoms of said one bond axis specified from the input part; and
said modifying part makes the free rotation around the atom by an angle specified from the input part, by making a free rotation around an atom located on an end, of the specified bond axis, other than the target of the coordinate modification, based on said one bond axis or, said one bond axis and one of two terminal atoms of said one bond axis in the ball-and-stick format.

3. The molecule design support apparatus as claimed in claim 1, wherein:
said determining part determines the end that is to become the target of the coordinate modification with respect to the bond axis, based on one bond axis of the molecule or, said one bond axis and one of two terminal atoms of said one bond axis in the ball-and-stick format specified from the input part; and said modifying part makes the rotation around the specified bond axis by an angle specified from the input part, by making the rotation around the specified bond axis, based on said one bond axis or, said one bond axis and said one of the two terminal atoms of said one bond axis.

4. The molecule design support apparatus as claimed in claim 1, wherein:

said determining part determines the end that is to become the target of the coordinate modification with respect to the molecule in its entirety, based on two continuous bond axes of the molecule or, said two continuous bond axes and one of two terminal atoms of said two continuous bond axes in the ball-and-stick format specified from the input part; and said modifying part makes a modification of the angle between two specified bond axes by an angle specified from the input part, by modifying an angle between said two continuous bond axes, based on said two continuous bond axes or, said two continuous bond axes and one of the two terminal atoms of said two continuous bond axes in the ball-and-stick format.

5. The molecule design support apparatus as claimed in claim 1, wherein:

said determining part determines the end that is to become the target of the coordinate modification with respect to the molecule in its entirety, based on three continuous bond axes of the molecule or, said three continuous bond axes and one of two terminal atoms of said three continuous bond axes in the ball-and-stick format specified from the input part; and said modifying part makes a rotation of the dihedral angle around a center bond axis of the three specified continuous bond axes by an angle specified from the input part, by rotating the center bond axis of said three continuous bond axes, based on said three continuous bond axes or, said three continuous bond axes and one of the two terminal atoms of said three continuous bond axes in the ball-and-stick format.

6. The molecule design support apparatus as claimed in claim 1, wherein:

said determining part determines the end that is to become the target of the coordinate modification with respect to the bond axis, based on one bond axis of the molecule or, said one bond axis and one of two terminal atoms of said one bond axis in the ball-and-stick format specified from the input part; and said modifying part makes an expansion and contraction of the specified bond axis by a contraction scale specified from the input part, based on said one bond axis or, said one bond axis and one of the two terminal atoms of said one bond axis in the ball-and-stick format.

7. The molecule design support apparatus as claimed in claim 1, wherein said determining part sets, as the target of the coordinate modification, only a bond axis set having a smaller bond axis number, from among a plurality of bond axis sets including bond axes linked to a bond axis other than the specified bond axis, with respect to two terminal atoms of the specified bond axis, when only the bond axis or continuous bond axes are specified from the input part.

8. The molecule design support apparatus as claimed in claim 1, wherein said determining part sets, as the target of the coordinate modification, only a bond axis set including bond axes linked to a bond axis other than the specified bond axis using a specified atom or an atom that is not specified as a base point, when the bond axis or continuous bond axes are specified from the input part and one of two terminal atoms of the specified bond axis is further specified from the input part.

9. The molecule design support apparatus as claimed in claim 1, wherein said determining part excludes from the target of the coordinate modification a bond axis set including bond axes linked to a bond axis other than the specified bond axis with respect to one of two terminal atoms of the bond axis or continuous bond axes specified from the input part, when the bond axis set includes a bond axis linked to a bond axis other than the specified bond axis with respect to the other terminal atom of the bond axis or continuous bond axes specified from the input part.

10. A non-transitory computer-readable storage medium which stores a program for causing a computer, having an input part, to realize a molecule design support function, said program comprising:

a storing procedure causing the computer to store in a storage part, with respect to data having a given three-dimensional molecular structure, an atom data structure A related to an atom, a bond axis data structure B related to a bond axis, and a molecule data structure M related to a molecule;

wherein the atom data structure A includes an identification number "a" made up of an atomic sequence number in internal coordinates, an atom number made up of a chemical symbol, a bond axis number made up of a numerical value that varies when an arbitrary new molecular structure is added to an original molecule, an identification number of the bond axis, made up of a set data of an identification number "b" of each bond axis included in the bond axis number, and an identification flag for use in checking whether or not the molecular structure has a ring structure, wherein the bond axis data structure B includes an identification number "b" made up of the number that is necessary to make all of the bond axes correspond 1:1 with each other, an identification number of a terminal atom, made up of a set data of the identification number "a" of the atom existing at both terminals of the bond axis, and having a data number is 2, an event flag indicating a present type of event with respect to events of the molecular structure forming a GUI (Graphical User Interface), including a rotation operation, an expansion and contraction operation, a delete operation, an add operation and a replace operation, an identification flag identical to the identification flag of the atom data structure A, and vector information including information indicating a 1:1 correspondence between the bond axis and a three-dimensional vector, wherein the molecule data structure M includes the atom number, the bond axis number, the atom data structure A, the bond axis data structure B, event information of the event, and the event flag, a determining procedure causing the computer to determine, in the three-dimensional molecular structure that is displayed by a half vector format or a ball-and-stick format on a screen of a display, an end that is to become a target of a coordinate modification with respect to a molecule in its entirety, in response to a bond axis of the molecule specified from the input part;

a modifying procedure causing the computer to make a modification of the molecular structure based on the specified bond axis and the end that is the target of the coordinate modification, using information included in the atom data structure A and the bond axis data structure B, in response to the modification specified from the input part, said modification including at least one of a free rotation around an atom, a rotation around a bond axis, an angular modification between two axes, a modification of a dihedral angle, and an expansion and contraction of a bond axis; and a display procedure causing the computer to display a modified molecular structure on the screen of the display based on a determination made by the determining procedure and the modification made by the modifying procedure.

11. The non-transitory computer-readable storage medium as claimed in claim 10, wherein:

said determining procedure causes the computer to determine the end that is to become the target of the coordinate modification with respect to the molecule in its entirety, based on one bond axis of the molecule or, said one bond axis and one of two terminal atoms of said one bond axis specified from the input part; and said modifying procedure causes the computer to make the free rotation around the atom by an angle specified from the input part, by making a free rotation around an atom located on an end, of the specified bond axis, other than the target of the coordinate modification, based on said one bond axis or, said one bond axis and one of two terminal atoms of said one bond axis in the ball-and-stick format.

12. The non-transitory computer-readable storage medium as claimed in claim 10, wherein:

said determining procedure causes the computer to determine the end that is to become the target of the coordinate modification with respect to the bond axis, based on one bond axis of the molecule or, said one bond axis and one of two terminal atoms of said one bond axis in the ball-and-stick format specified from the input part; and said modifying procedure causes the computer to make the rotation around the specified bond axis by an angle specified from the input part, by making the rotation around the specified bond axis, based on said one bond axis or, said one bond axis and said one of the two terminal atoms of said one bond axis.

13. The non-transitory computer-readable storage medium as claimed in claim 10, wherein:

said determining procedure causes the computer to determine the end that is to become the target of the coordinate modification with respect to the molecule in its entirety, based on two continuous bond axes of the molecule or, said two continuous bond axes and one of two terminal atoms of said two continuous bond axes in the ball-and-stick format specified from the input part; and said modifying procedure causes the computer to make a modification of the angle between two specified bond axes by an angle specified from the input part, by modifying an angle between said two continuous bond axes, based on said two continuous bond axes or, said two continuous bond axes and one of the two terminal atoms of said two continuous bond axes in the ball-and-stick format.

14. The non-transitory computer-readable storage medium as claimed in claim 10, wherein:

said determining procedure causes the computer to determine the end that is to become the target of the coordinate modification with respect to the molecule in its entirety, based on three continuous bond axes of the molecule or, said three continuous bond axes and one of two terminal atoms of said three continuous bond axes in the ball-and-stick format specified from the input part; and said modifying procedure causes the computer to make a rotation of the dihedral angle around a center bond axis of the three specified continuous bond axes by an angle specified from the input part, by rotating the center bond axis of said three continuous bond axes, based on said three continuous bond axes or, said three continuous bond axes and one of the two terminal atoms of said three continuous bond axes in the ball-and-stick format.

15. The non-transitory computer-readable storage medium as claimed in claim 10, wherein:

said determining procedure causes the computer to determine the end that is to become the target of the coordinate modification with respect to the bond axis, based on one bond axis of the molecule or, said one bond axis and one of two terminal atoms of said one bond axis in the ball-and-stick format specified from the input part; and said modifying procedure causes the computer to make an expansion and contraction of the specified bond axis by a contraction scale specified from the input part, based on said one bond axis or, said one bond axis and one of the two terminal atoms of said one bond axis in the ball-and-stick format.

16. The non-transitory computer-readable storage medium as claimed in claim 10, wherein said determining procedure causes the computer to set, as the target of the coordinate modification, only a bond axis set having a smaller bond axis number, from among a plurality of bond axis sets including bond axes linked to a bond axis other than the specified bond axis, with respect to two terminal atoms of the specified bond axis, when only the bond axis or continuous bond axes are specified from the input part.

17. The non-transitory computer-readable storage medium as claimed in claim 10, wherein said determining procedure causes the computer to set, as the target of the coordinate modification, only a bond axis set including bond axes linked to a bond axis other than the specified bond axis using a specified atom or an atom that is not specified as a base point, when the bond axis or continuous bond axes are specified from the input part and one of two terminal atoms of the specified bond axis is further specified from the input part.

18. The non-transitory computer-readable storage medium as claimed in claim 10, wherein said determining procedure causes the computer to exclude from the target of the coordinate modification a bond axis set including bond axes linked to a bond axis other than the specified bond axis with respect to one of two terminal atoms of the bond axis or continuous bond axes specified from the input part, when the bond axis set includes a bond axis linked to a bond axis other than the specified bond axis with respect to the other terminal atom of the bond axis or continuous bond axes specified from the input part.

* * * * *